(12) United States Patent
Naidu

(10) Patent No.: US 7,375,080 B1
(45) Date of Patent: *May 20, 2008

(54) IMMOBILIZED LACTOFERRIN (IM-LF) ANTIMICROBIAL AGENTS AND USES THEREOF

(76) Inventor: A. Satyanarayan Naidu, 22810 Mountain Laurel Way, Diamond Bar, CA (US) 91765

( * ) Notice: Subject to any disclaimer, the term of this patent is extended or adjusted under 35 U.S.C. 154(b) by 0 days.

This patent is subject to a terminal disclaimer.

(21) Appl. No.: 09/980,062

(22) PCT Filed: May 26, 2000

(86) PCT No.: PCT/US00/14818

§ 371 (c)(1), (2), (4) Date: May 10, 2002

(87) PCT Pub. No.: WO00/72690

PCT Pub. Date: Dec. 7, 2000

Related U.S. Application Data

(63) Continuation-in-part of application No. 09/322,700, filed on May 28, 1999, now Pat. No. 6,172,040.

(51) Int. Cl.
*A23B 4/20* (2006.01)
*A23L 3/3499* (2006.01)
*A23L 3/3526* (2006.01)
*A61K 38/40* (2006.01)
*A61L 2/18* (2006.01)

(52) U.S. Cl. ............................. 514/6; 422/28; 422/32; 426/310; 426/322; 426/326; 426/332; 426/335; 426/532; 514/8; 514/21

(58) Field of Classification Search ................ 424/439, 424/442; 426/302, 310, 321, 322, 326, 332, 426/335, 532, 574, 652; 422/28, 32; 514/6, 514/8, 21; 530/395, 400, 810, 811, 812, 530/813, 814, 815, 816, 817

See application file for complete search history.

(56) References Cited

U.S. PATENT DOCUMENTS

| | | | | |
|---|---|---|---|---|
| 4,791,193 A | * | 12/1988 | Okonogi et al. ............. | 530/416 |
| 5,206,156 A | * | 4/1993 | Samain et al. ............... | 435/101 |
| 6,066,469 A | * | 5/2000 | Kruzel et al. ............... | 435/69.1 |
| 6,172,040 B1 | * | 1/2001 | Naidu ........................... | 514/6 |
| 6,444,823 B1 | * | 9/2002 | Biedermann et al. ....... | 546/208 |
| 6,475,511 B2 | * | 11/2002 | Gohlke et al. .............. | 424/441 |
| 2003/0229011 A1 | * | 12/2003 | Braun et al. .................. | 514/6 |
| 2005/0025729 A1 | * | 2/2005 | Groteluschen et al. ........ | 424/63 |

FOREIGN PATENT DOCUMENTS

| | | | |
|---|---|---|---|
| EP | 389795 A | * | 10/1990 |
| EP | 629347 A | * | 12/1994 |
| EP | 753308 A | * | 1/1997 |
| EP | 753309 A | * | 1/1997 |
| GB | 443911 A | * | 3/1936 |
| JP | 07300425 A | * | 11/1995 |
| RU | 2099065 C1 | * | 12/1997 |
| WO | WO-91/13982 A1 | * | 9/1991 |

OTHER PUBLICATIONS

Harper et al. Dairy Technology and Engineering. Westport: The AVI Publ. Co., Inc. pp. 20-23, 28-37. 1976.*
Naidu et al. Milk Lactoferrin—Natural Microbial Blocking Agent (MBA) For Food Safety. Environmental & Nutritional Interactions. 1998, vol. 2, pp. 35-50.*

* cited by examiner

*Primary Examiner*—Jeffrey Edwin Russel
(74) *Attorney, Agent, or Firm*—Lee, Hong, Degerman, Kang & Schmadeka

(57) ABSTRACT

Disclosed is a composition of matter comprising a defined dispersion of lactoferria immobilized on a naturally occuring substrate via the N-terminus region of the lactoferrin. Compositions comprising immobilized lactoferrin (Im-LF) are used in a method for reducing the microbial contamination of a composition subject to microbial contamination, which is also disclosed, and which encompasses a method for reducing the microbial contamination of a foodstuff, such as a meat product. Foodstuffs treated by the method are disclosed, including meat products. A method of inhibiting the growth and/or adhesion of a microbial species on a food-contacting surface f a material for food packaging or food handling with Im-LF is also disclosed. Food containers and food-handling implements so treated are also disclosed, as are antimicrobial cleansers, polishes, paints, sprays, soaps, or detergents containing Im-LF for applying to an inanimate surface.

53 Claims, No Drawings

IMMOBILIZED LACTOFERRIN (IM-LF) ANTIMICROBIAL AGENTS AND USES THEREOF

This application is the National Stage Entry of PCT/US00/14818 filed May 26, 2000 which is a continuation in part of U.S. patent application Ser. No. 09/322,700 filed May 28, 1999, now U.S. Pat. No. 6,172,040.

BACKGROUND OF THE INVENTION

1. Field of the Invention

This invention relates to antimicrobial agents and their use.

2. Discussion of the Related Art

Antimicrobial agents are used in the treatment of infections, particularly of the gastrointestinal tract. Gastrointestinal infections affect millions of people world-wide, especially children. Infantile gastroenteritis affects more than 20 million children below twelve months age worldwide annually and considered a leading cause of mortality. Intestinal infections in children, unassociated with antibiotic use or hospital stays, can cause chronic diarrhea and failure to grow. (E.g., T. E. Liston, *Clostridium difficile toxin associated with chronic diarrhea and failure to gain weight*, Clin. Pediatr. (Phila.) 22(6):458-60 [1983]). Toxic shock, or bacteraemia and subsequent sepsis are other possible complications of intestinal infection. (See, e.g., P. Naaber et al., *Bacterial translocation, intestinal microflora and morphological changes of intestinal mucosa in experimental models of Clostridium difficile infection*, J. Med. Microbiol. 47(7):591-98 [1998]). Enterotoxigenic bacterial strains are linked with a significant number of cases of antibiotic-associated diarrhea, especially among the elderly, children, and infants. Gastrointestinal infections also pose an increasing health hazard in hospital settings.

Of course, bacteria inhabit healthy intestines to the benefit of their human and animal hosts. But pathogenic bacterial strains and opportunistic pathogens that can infect immunocompromised hosts have an adverse disease-causing effect.

Prominent agents of microbial disease include *Clostridium* species, especially *C. difficile* and *C. perfringens*. *Clostridium* species are gram-positive, spore-forming anaerobes; some strains that colonize the human intestines can, under certain circumstances, release potent protein exotoxins that induce inflammation of the intestinal mucosa. (M. L. Job and N. F. Jacobs, Jr., *Drug-induced Clostridium difficile-associated disease*, Drug Saf.17(1):3746 [1997]). For example, antibiotics and other chemotherapeutic agents can induce the expression of Toxins A and B from *Clostridium difficile*. (B. A. Cunha [1998]). Agents known to have a high potential to induce *C. difficile*-associated disease are aminopenicillins, cephalosporins and clindamycin. (M. L. Job and N. F. Jacobs, Jr., *Drug-induced Clostridium difficile-associated disease*, Drug. Saf. 17(1):37-46 [1997]; Y. Hutin et al., *Prevalence of and risk factors for Clostridium difficile colonization at admission to an infectious diseases ward*, Clin. Infect. Dis. 24(5):920-24 [1997]; C. D. Settle and M. H. Wilcox [1996]).

In developed countries, the great majority of cases of *C. difficile* infection are hospital-acquired, and the number of nosocomial clostridial infections is reported to be rising. (C. D. Settle and M. H. Wilcox, *Review article: antibiotic-induced Clostridium difficile infection*, Aliment. Pharmacol. Ther. 10(6): 83541[1996]; J. S. Brazier, *The epidemiology and typing of Clostridium difficile*, J. Antimicrob. Chemother. 41 Suppl. C: 47-57 [1998]; S. Tabaqchali and M. Wilks, *Epidemiological aspects of infections caused by Bacteroides fragilis and Clostridium difficile*, Eur. J. Clin. Microbiol. Infect. Dis. 11(11): 1049-57 [1992]; C. R. Clabots et al., *Acquisition of Clostridium difficile by hospitalized patients: evidence for colonized new admissions as a source of infection*, J. Infect. Dis. 166(3):561-67 [1992]).

A nosocomial pleural infection with *C. difficile*, following surgical insertion of a chest drain has also been reported (A. J. Simpson et al., *Nosocomial empyema caused by Clostridium difficile*, J. Clin. Pathol. 49(2):172-73 [1996]), but intestinal infections are the greatest problem.

Nosocomial diarrhea due to gastrointestinal infection with *C. difficile* has become a major health care problem, causing 20-30% of all nosocomial diarrheas and affecting up to 8% of hospitalized patients. (L. R. Peterson and P. J. Kelly, *The role of the clinical microbiology laboratory in the management of Clostridia difficile-associated diarrhea*, Infect. Dis. Clin. North Am. 7(2):277-93 [1993]). *Clostridium difficile* is considered to be the premier cause of diarrhea among hospitalized patients. (M. Delmee et al., *Treatment of Clostridium difficile colitis. Summary of a round table held in Brussels on Mar.* 3, 1994, Acta Clin. Belg. 50(2):114-116 [1995]).

In developing countries, *C. difficile* is also thought to be a causal agent of wide-spread acute diarrheal disease. (S. K. Niyogi et al., *Prevalence of Clostridium difficile in hospitalized patients with acute diarrhea in Calcutta*, J. Diarrhoeal Dis. Res. 9(1):16-19 [1991]; S. Q. Akhtar, *Isolation of Clostridium difficile from diarrhea patients in Bangladesh*, J. Trop. Med. Hyg. 90(4):189-92 [1987]).

Enterotoxigenic strains of *C. perfringens* are linked with a significant number of cases of antibiotic-associated diarrhea, especially among elderly hospitalized patients, children, and infants. (A. Wada et al., *Nosocomial diarrhea in the elderly due to enterotoxigenic Clostridium perfringens*, Microbiol. Immunol. 40(10):767-71 [1996]; M. M. Brett et al., *Detection of Clostridium perfringens and its enterotoxin in cases of sporadic diarrhea*, J. Clin. Pathol. 45(7):609-11 [1992]; S. C. Samuel et al., *An investigation into Clostridium perfringens enterotoxin-associated diarrhea*, J. Hosp. Infect. 18(3):219-30 [1991]; S. P. Boriello et al., *Epidemiology of diarrhea caused by enterotoxigenic Clostridium perfringens*, J. Med. Microbiol. 20(3):363-72 [1985]; R. Willliams et al., *Diarrhoea due to entertoxigenic Clostridium perfringens: clinical features and management of a cluster of* 10 *cases*, Age Ageing 14(5):296-302 [1985]). *Clostridium perfringens* has been implicated as a possible contributor to sudden infant death syndrome (SIDS) in susceptible infants. (R. R. Meer et al., *Human disease associated with Clostridium perfringens enterotoxin*, Rev. Environ. Contam. Toxicol. 150:75-94 [1997]).

*Clostridium perfringens* is well known as a causative agent of non-gastrointestinal gangrene, a special problem for many elderly and diabetic patients with poor blood circulation. But also in more extreme cases of gastrointestinal infection, *C. perfringens* can cause enteritis necroticans, a gangrene of the bowel resulting in necrosis, sepsis, and hemolysis, in humans and domesticated animals. (L. E. Clarke et al., *Enteritis necroticans with midgut necrosis caused by Clostridium perfringens*, Arch. Surg. 129(5):557-60 [1994]; D. Bueschel et al., *Enterotoxigenic Clostridium perfringens type A necrotic enteritis in a foal*, J. Am. Vet. Med. Assoc. 213(9):1305-07 [1998]; E. G. Pearson et al., *Hemorrhagic enteritis caused by Clostridium perfringens type C in a foal*, J. Am. Vet. Med. 188(11): 1309-10 [1986]; F. Al-Sheikhy and R. B. Truscott, *The interaction of* clostridium perfringens and its toxins in the production of necrotic enteritis of chickens, Avian Dis. 21(2):256-63 [1977]).

Although rare in developed countries, clostridial enteritis necroticans in humans is more common in some developing countries. (D. A. Watson et al., *Pig-bel but no pig: enteritis necroticans acquired in Australia*, Med. J. Aust. 155(1):47-50 [1991]). In New Guinea, enteritis necroticans, known locally as pigbel, has been a major cause of illness and death among children. (G. W. Lawrence et al., *Impact of active immunisation against enteritis necroticans in Papua New Guinea*, Lancet 336(8724):1165-67 [1990]). *Clostridium perfringens* type C, the etiologic agent of enteritis necroticans, was also isolated from Bangladeshis with bloody or watery diarrheal illness. (F. P. van Loon et al., *Clostridium perfringens type C in bloody and watery diarrhea in Bangladesh*, Trop. Geogr. Med. 42(2):123-27 [1990]).

Entertoxigenic strains of *C. perfringens* have also been linked to nosocomial and non-nosocomial outbreaks of food poisoning, due to heat-resistant spores and a rapid growth rate in warm food. (A. M. Pollack and P. M. Whitty, *Outbreak of Clostridium perfringens food poisoning*, J. Hosp. Infect. 17(3):179-86 [1991]; M. Van Darnme-Jongsten et al., *Synthetic DNA probes for detection of enterotoxigenic Clostridium perfringens strains isolated from outbreaks of food poisoning*, J. Clin. Microbiol. 28(1):131-33 [1990]).

Spores of *Clostridium botulinum* germinating in warm food can cause another form of food poisoning called botulism. Growing particularly in non-acidic foods lacking nitrites, and protected from oxygen, the vegetative cells of *C. botulinum* release an exotoxin that when consumed with the food is activated by trypsin in the stomach, and is absorbed intact by the blood stream. The exotoxin binds to nerve cells, preventing the release of the neurotransmitter acetylcholine. Resulting symptoms of botulism include blurred vision, difficulty in swallowing and speaking, and increasing muscular weakness, and usually nausea and vomiting. Death often results from paralysis of the muscles required for breathing. (R. Y. Stanier et al., *The Microbial World*, 5th ed., Prentice Hall, Englewood Cliffs, N.J., pp. 626-27 [1986]). *Clostridium botulinum* sometimes colonizes the intestines of infants and can cause infantile botulism, which can lead to respiratory paralysis and sudden infant death.

Botulism is a problem for the food packaging industry. Spores of *C. botulinum* may not be killed if canning is done at too low a temperature. High temperature autoclave treatment may be unsuitable for some foods Mayonnaise and other non-acidic foods are particularly prone to foster the growth of *C. botulinum*. Now with increasing health concerns about the use of nitrite as a food preservative, alternative antimicrobial agents are needed against the growth of *C. botulinum* and other food poisoning bacterial pathogens.

Of course, a wide variety of microbes, beside pathogenic *Clostridium* spp., poses problems of contamination and infection. These include bacteria such as enterotoxigenic *Escherichia coli*, enteropathogenic *Escherichia coli*, verotoxic *Escherichia coli*, including serotype O157:H7, *Shigella dysenteriae*, *Shigella flexneri*, *Salmonella typhimurium*, *Salmonella abony*, *Salmonella dublin*, *Salmonella hartford*, *Salmonella kentucky*, *Salmonella panama*, *Salmonella pullorum*, *Salmonella rostock*, *Salmonella thompson*, *Salmonella virschow*, *Campylobacter jejuni*, *Aeromonas hydrophila*, *Staphylococcus aureus*, *Staphylococcus hyicus*, *Staphylococcus epidermidis*, *Staphylococcus hominis*, *Staphylococcus warneri*, *Staphylococcus xylosus*, *Staphylococcus chromogenes*, *Bacillus cereus*, *Bacillus subtilis*, *Candida albicans*, and such radiation-resistant bacteria as: *Brochothrix thermospacta*, *Bacillus pumilus*, *Enterococcus faecium*, *Deinococcus radiopugnans*, *Deinococcus radiodurans*, *Deinobacter grandis*, *Acinetobacter radioresistens*, *Methylobacterium radiotolerans*, as well as other kinds of bacteria. Various pathogenic fungi, protozoa and viruses are also microbes that are often difficult to treat with known antimicrobial agents.

Antimicrobial agents with selective toxicity for a specific spectrum or range of pathogenic microorganisms are well known in the art. One class of antimicrobial agents is the antibiotics, which are compounds, synthesized and excreted by various microorganisms, that are selectively toxic to other microorganisms, specifically bacteria. In addition, some antibiotics can be artificially modified to produce antimicrobial agents that are more effective and/or more able to overcome antibiotic resistance.

Antimicrobial agents with selective toxicity for a specific spectrum or range of pathogenic microorganisms are well known in the art. One class of antimicrobial agents is the antibiotics, which are compounds, synthesized and excreted by various microorganisms, that are selectively toxic to other microorganisms, specifically bacteria. In addition, some antibiotics can be artificially modified to produce antimicrobial agents that are more effective and/or more able to overcome antibiotic resistance.

One of the most commonly used antibiotics for the treatment of gastrointestinal infections or bacterial overgrowths is vancomycin. Like many antimicrobial agents, vancomycin is prohibitively expensive, especially for developing countries, and there are concerns about the rapid development of vancomycin-resistance among pathogenic *Clostridium*, *Enterococcus*, *Pediococcus*, *Citrobacter*, *Klebsiella*, *Enterobacter*, and *Staphylococcus* species, because the plasmid-borne vancomycin resistance gene (VanR) is readily transmissible. (*ASHP therapeutic position statement on the preferential use of metronidazole for the treatment of Clostridium difficile-associated disease*, Am. J. Health Syst. Pharm. 55(13): 1407-1 [1998]; S. H. Cohen et al., *Isolation of a toxin B-deficient mutant strain of Clostridium difficile in a case of recurrent C. difficile-associated diarrhea*, Clin. Infect. Dis. 26(2): 1250 [1998]; C. Edlund et al., *Effect of vancomycin on intestinal flora of patients who previously received antimicrobial therapy*, Clin. Infect. Dis. 25(3):729-32 [1997]; C. A. O'Donovan et al., *Enteric eradication of vancomycin-resistant Enterococcus faecium with oral bacitracin*, Diagn. Microbiol. Infect. Dis. 18(2):105-09 [1994]; E. Yamaguchi et al., *Colonization pattern of vancomycin-resistant Enterococcus faecium*, Am. J. Infect. Control 22(4):202-06 [1994]; C. P. Kelly and J. T. LaMont [1998]). The phenomenon of antibiotic resistance, by no means limited to vancomycin-resistance, is an increasing public health problem.

Accordingly, there remains a definite need for a modestly priced antimicrobial agent for treating gastrointestinal and other infections, without the commonly unpleasant side effects and bacterial resistance often associated with vancomycin and other antibiotics.

Meat animals and egg laying hens often carry, among their native gastrointestinal microflora and/or within their lymph nodes, bacteria associated with food-poisoning and gastrointestinal disease in humans, for example various *Salmonella* species. (E.g., Letellier, A. et al., *Assessment of various treatments to reduce carriage of Salmonella in swine*, Can. J. Vet. Res. 64(1):27-31 [2000]). Some pathogenic bacteria, such as *Salmonella enteritidis*, can invade the reproductive organs of egg layers and ultimately contaminate egg contents. (E.g., Seo, K. H. et al., *Combined effect of antibiotic and competitive exclusion treatment on Salmonella enteritidis fecal shedding in molted laying hens*, J. Food Prot. 63(4):545-48 [2000]).

With respect to the meat, the edible tissues of a healthy meat animal are essentially sterile prior to slaughter. Various innate host defense mechanisms at the external and internal organ surfaces create an effective barrier and prevent microorganisms from invading the tissues of a live animal. As soon as the animal is slaughtered, however, the natural defenses against invading microbes virtually disappear, and the exposed tissues become highly susceptible to microbial colonization and proliferation. Meat of the freshly slaughtered animal is prone to contamination with a variety of bacterial species, influenced by the degree of sanitation practiced during the meat processing and packing operations.

The economic impact of food-borne pathogenic outbreaks and the shorter than desired shelf life of refrigerated products, even vacuum packaged refrigerated products, has necessitated the search for an effective antimicrobial system for the meat industry. The recent occurrence of verotoxic *Escherichia coli* (*E. coli*) serotype O157:H7 in ground beef causing hemolytic uremic syndrome highlighted this long-standing problem, in foods and, especially, meats. It has prompted a major review of safety issues in the food industry and a call for improved methods for preventing microbial contamination. Various methods are currently in practice to control *E. coli* and other microbial contamination in foods, but, unfortunately, they suffer from a variety of drawbacks.

For example, in the meat industry, acid washing of beef carcasses is currently being employed as a microbial intervention. However, recent studies have shown that certain types of *E. coli*, such as the verotoxic strains of serotype O157:H7 and vancomycin-resistant strains of *Enterococcus faecium*, can survive acid conditions, while at the same time produce harmful toxins. The meat industry is also irradiating meat in an attempt to control pathogens and food spoilage organisms. However, studies have shown that although irradiation appears to be effective at killing some types of *Escherichia coli*, there are still various other microorganisms, including strains of *Brochothrix thermospacta* and *Bacillus pumilus*, known to be radiation resistant and thus are able to survive such processes. Irradiation also can produce undesirable changes in the texture and/or organoleptic quality of beef. Further, both of these methods are cidal processes that kill microorganisms leaving endotoxins, microbial debris and other proinflammatory substances which can cause undesirable immunological reactions in the host. Finally, neither of these methods excludes the possibility of post-processing contamination once the beef is treated for microbial contaminants.

In addition to food-borne pathogens, microbial spoilage of packaged foods, including fresh meats and vegetable foods, is a significant concern to the food industry. Under certain conditions, it is possible to control microbes, including enteric pathogens, using such well known antimicrobial agents as acids, salts, oxidative agents, antibiotics, bacteriocins, and the like. Typically, the mode of action of these agents is "cidal"—the direct killing of the microbes, or "stasis"—the inhibition of microbial growth/multiplication. Another mode of action for conventional antimicrobial agents is opsonization. The agents intervene by promoting microbial phagocytosis by macrophages.

Certain cellular research relating to the mechanisms of microbial biosurface interactions has led to the identification of another mode of action, microbial blocking, and a new class of antimicrobial agents, microbial blocking agents (MBAs). MBAs are naturally occurring biological substances that block microbial adhesion-colonization, retard growth-multiplication, and neutralize the adverse effects of proinflammatory cell debris.

It has not proved possible to apply such microbial blocking agents during meat packing or other food processing conditions, because of the difficulty of delivering a biofunctionally active and structurally stable MBA to the food product to be treated. The difficulty is compounded when the food product is a meat product, because a controlled milieu is required for a broad-spectrum activity of MBA to block various microorganisms on a chemically complex and heterogenous meat tissue.

Breast-fed infants are better protected against various gastrointestinal infections than the formula-fed infants. Lactoferrin is one of the major antimicrobial systems in milk and colostrum and has been credited for protection of newborns against gastrointestinal illness. However, deficiency or dysfunction of lactoferrin and/or other antimicrobial systems may exist in certain breast milks depending on the nutritional and health status of feeding mothers.

Lactoferrin (LF) is an iron-binding glycoprotein present in milk and various mammalian secretions (e.g. saliva, tears, mucus, and seminal fluids). Crystallographic studies of LF indicate a bilobate structure (N-terminus and C-terminus lobes) with one iron-binding site in each lobe. LF has ability to reversibly bind two $Fe^{3+}$ ions per lobe in coordination with two $CO_3^{2-}$ ions. LF can release the bound iron in a fully reversible manner, either on exposure to lowered pH (below 4.0) or on receptor binding. This high affinity for iron is linked to many of its biological functions including antimicrobial effects. Various laboratory studies have reported that the structural integrity of LF is critical for its antimicrobial effects against bacteria, fungi, protozoa, and viruses.

However, the activity of LF, like the activity of most proteins, is highly dependent on the three-dimensional or tertiary structure of the protein. If the protein does not have the proper conformation its activity is diminished or lost. LF's instability limits it usefulness. Milieu conditions such as metals (iron in particular), carbonic ions, salts, pH and conductivity affect the antimicrobial properties of LF. In addition, protein isolation procedures, storage, freezing-thawing, can adversely affect the biofunctionality of LF. Consequently, before LF can be used for commercial application, it would be expected to become denatured or inactivated, and lose its antimicrobial properties.

In fact, under certain conditions, when the LF molecule is degraded or denatured, cationic peptide fragments are generated. These cationic peptide fragments exhibit a non-specific antimicrobial activity, making them absolutely unsuitable as an ingredient in a food product. The consumer of a food product does not want to ingest a non-specific antimicrobial agent, because of the agent's adverse affect on the desirable microbes always present in a human body, particularly within the gastrointestinal tract.

Thus, an antimicrobial agent is needed for blocking microbial contamination in foods, meats and seafood in particular, on non-biological surfaces, on biological surfaces, and in biological fluids, whether in vivo or in vitro, that does not pose the undesired affects of cidal antimicrobial systems but that also exhibits carry through properties for the prevention of post-processing contamination.

SUMMARY OF THE INVENTION

The present invention includes compositions of matter comprising a defined dispersion of lactoferrin (LF) immobilized on a naturally occurring substrate via the amino-terminus (N-terminus) region of the lactoferrin. Such substrates include organic compounds, which attach to the LF peptide at the amino-terminus (N-terminus), leaving the carboxy-terminal (C-terminal) end of the LF peptide free to interact with microbes. The inventive compositions containing immobilized lactoferrin (herein also referred to as "Im-LF") are effective in treating a wide variety of microbes including bacteria, fungi, protozoa and viruses. Thus, the present invention is directed to the use of Im-LFs as antimicrobial agents for reducing or inhibiting microbial growth, infection, adhesion, and/or contamination in, or on, foodstuffs and inanimate or non-biological surfaces, in a human or non-human vertebrate, in the gastrointestinal tract or in, or on, any other body site or tissue, or on biological surfaces or in biological fluids, whether in vivo or in vitro.

In some embodiments of the invention, compositions containing Im-LF are useful in an inventive method for reducing or inhibiting microbial contamination of a composition subject to microbial contamination, for example, a foodstuff, such as, but not limited to, a meat product (e.g., a beef, pork or poultry product). The method involves treating the composition subject to microbial contamination with a sufficient amount of isolated lactoferrin immobilized on a naturally occurring substrate via the N-terminus region of the lactoferrin, to reduce or inhibit contamination of the composition by microbes. A sufficient amount of Im-LF, optionally combined with native lactoferrin, is used in the method to treat the product and thereby reduce or inhibit microbial contamination thereof. The inventive method is useful for inhibiting food spoilage and reducing the risk of food poisoning to consumers. Foodstuffs treated by the method are also provided by the present invention. The inventive method for inhibiting microbial growth in a foodstuff and inventive foodstuffs, employing the antimicrobial properties of Im-LF, are useful alternative means of preventing food contamination.

In addition, an inventive method of inhibiting the growth and/or adhesion of a microbial species on a foodstuff is also provided. The method involves treating a food-contacting surface of a material for food packaging or food handling with an Im-LF; and contacting a foodstuff with the surface, whereby the growth of a microbial species on the foodstuff is inhibited, compared to the use of like food packaging or foodhandling materials without Im-LF. Also provided is a food container or food-handling implement, having a food-contacting surface treated with an Im-LF in an amount effective to inhibit the growth of a microbial species on the surface.

The present invention also includes antimicrobial cleansers, polishes, paints, sprays, soaps, or detergents for applying to inanimate surfaces, including non-biological surfaces. The cleansers, polishes, paints, sprays, soaps, or detergents contain Im-LF in an amount effective to inhibit the growth of a microbial species on the surface.

Alternative embodiments of the inventive compositions contain at least one pharmaceutically acceptable carrier, in addition to isolated lactoferrin immobilized on a naturally occurring substrate via the N-terminus region of the lactoferrin. These embodiments include cosmetics (e.g., lipsticks, glosses, eye shadows and liners, rouge, body paints), cleansers (e.g., skin cleansers), food supplements, and medicaments. The inventive compositions suitably formulated are also useful for preventing or inhibiting microbial infections and/or overgrowths, for example, small intestinal bacterial overgrowth (SIBO), in or on a vertebrate subject, such as a human or a non-human vertebrate.

In particular, an inventive method of inhibiting the growth and/or adhesion of a microbe in, or on, a vertebrate subject involves administering to the subject a pharmaceutically acceptable composition comprising an isolated lactoferrin immobilized on a naturally occurring substrate via the N-terminus region of the lactoferrin, by a pharmaceutically acceptable delivery route. The Im-LF is thus delivered in a dose effective to prevent or inhibit the growth of a microbe in or on the subject.

Similarly, an inventive method of preventing or inhibiting the growth and/or adhesion of a microbe on a biological surface or in a biological fluid involves treating the biological surface or fluid with a pharmaceutically acceptable composition comprising an isolated lactoferrin immobilized on a naturally occurring substrate via the N-terminus region of the lactoferrin. Im-LF is delivered in an amount effective to inhibit the growth and/or adhesion of the microbe on the surface or in the fluid.

These and other advantages and features of the present invention will be described more fully in a detailed description of the preferred embodiments which follows.

DETAILED DESCRIPTION OF THE PREFERRED EMBODIMENTS

The inventive compositions contain a defined dispersion of lactoferrin (LF) immobilized on a naturally occurring substrate via the amino terminus (N-terminus) region of the lactoferrin molecule. The LF and immobilized lactoferrin (Im-LF) useful in accordance with the compositions and methods of the present invention include or contain glycosylated or unglycosylated LF peptides. The terms "LF", "LF protein", and "LF peptide" are used interchangeably herein. A full length LF peptide sequence has about 600 to about 800 contiguous amino acids. For example, native human LF is about 703 amino acids long; native bovine LF is about 651 amino acids long. Other useful mammalian LF sequences are of various but similar lengths. Useful LF peptides include full length native LF peptides and also include LF peptides lacking one to about eleven contiguous amino acids from the extreme end of the N-terminus region or the extreme end of the C-terminus region of a native LF peptide amino acid sequence. Also useful are LF peptides having sequences variant in one or more amino acid residues compared to a native LF sequence, but that remain at least partially functional. The term "functional", when used herein as a modifier of LF protein(s) or peptide(s), refers to a polypeptide that exhibits both the ability to bind at its N-terminus to a substrate, i.e., become immobilized, and also the antimicrobial activity attributed to native LF amino acid sequences. Thus, the term "native LF", in reference to mixtures of native LF and Im-LF, encompasses functional LF having a variant amino acid sequence.

The LF is immobilized on a naturally occurring substrate. Such substrates include organic compounds, which attach to the LF protein to the N-terminus. Most preferably, the substrate is a galactose-rich polysaccharide. Suitable galactose-rich polysaccharides include galactose derivatives comprising galactose, anhydrogalactose, 2-Ome-galactose, and 4-Ome-galactose, among others. The galactose-rich polysaccharides can be purchased or extracted from commercial agars by known methods. Other suitable biologically active substrates include proteins, such as collagen, denatured collagen (gelatin), fibronection, and casein; polysaccharides, such as mucin, heparan-sulfates, carrageenan; nucleic acids and their nucleotides, such as deoxyribonucleic acid and adenosine triphosphate; and lipids such as triglycerides.

The LF can be, but is not necessarily, of homologous origin with respect to the composition, product, or surface that is treated, or with respect to the vertebrate subject to which it is administered, in accordance with the present methods. Lactoferrins of heterologous mammalian origin with respect to the surface are also useful. Thus, for example, in accordance with the inventive method, an Im-LF of human origin functions to reduce or inhibit microbial contamination of meat or flesh of non-human origin, or functions to inhibit microbial growth in or on human and/or non-human vertebrates. Similarly, bovine Im-LF can be used to treat either bovine or non-bovine meat or meat products and is useful in cosmetics, cleansers, food supplements, or medicaments intended for human use or for bovine and/or non-bovine veterinary uses. However, for systemic delivery to human or non-human vertebrates, in vivo, homologous LF is preferred to avoid adverse immunoreactions.

The LF is immobilized on a naturally occurring substrate via the N-terminus region of the lactoferrin. Suitable substrates include proteins, polysaccharides, nucleic acids. Preferred substrates include collagen, fibronectin, casein, mucin, heparin sulfate, carrageenan, or deoxyribonucleic acid.

Most preferably, the substrate is a galactose-rich polysaccharide (GRP). Galactose-rich polysaccharides are known in the art as water-soluble extracts of agar that contain a majority of galactose residues and/or galactose derivatives, which can be substituted or non-substituted. (Gerlach, D. et al., *Identification of a novel lectin in Streptococcus pyogenes and its possible role in bacterial adherence to pharyngeal cells*, Current Microbiology 28:331-38 [1994]). Suitable galactose-rich polysaccharides include galactose derivatives comprising galactose, anhydrogalactose, 2-Ome-galactose, and 4-Ome-galactose, among others. Galactose-rich polysaccharides can also contain a minority of other sugar and non-sugar components, including residues of nitrogen-containing non-sugar compounds and/or sulfated residues. The galactose-rich polysaccharides can be purchased or extracted from commercial agars by known methods. (E.g., Gerlach, D. et al. [1994]; Naidu, A. S., *Agar*, Chapter 16, In: *Natural Food Antimicrobial Systems*, A. S. Naidu (ed.), CRC Press, Inc., pp. 417-27 [2000]).

Other suitable biologically active substrates include proteins, such as collagen, fibronectin, and casein; polysaccharides, such as mucin, heparin-sulfates, and carrageenan; and nucleic acids, such as deoxyribonucleic acid.

The LF is immobilized on the substrate using any suitable technique. For example, LF can be immobilized simply by mixing the LF with the biologically active substrate in a suitable medium, such as deionized water. The immobilization process is dependent on the quality of the substrate as well as the quality of the LF. For example, in most of the commercially available lactoferrins, there is variation in the level of impurities (range: 4-10%), degree of non-specific cidal activity (range: 20-40%), and extent of protein denaturation (range: 10-25%). Consequently, the amount of substrate and the amount of LF to be used in the immobilization reaction will depend, inter alia, on the choice of starting materials. The immobilization technique and the amounts of substrate and LF are readily determined by a skilled artisan without undue experimentation.

Immobilization neutralizes the cationic effect of LF peptide fragments, and eliminates the undesirable, non-specific cidal activity characteristic of lactoferricin. Without intending to be limited by a theory of operation, it is believed that immobilization gives structural stability and bio-functional specificity to the LF protein. This property facilitates the retention and carry-through of Im-LF, even, for example, when Im-LF is applied during an early stage of meat or other food processing.

In preferred embodiments of the inventive compositions and methods, the Im-LF is combined in a mixture with native LF. The molar ratio of immobilized versus native LF in such a mixture is important in providing broad-spectrum activity, and molecular stability of both the immobilized and the native LF. Mixtures of Im-LF and native LF in a ratio of from about 0.25:1 to about 1:10, preferably from about 1:1 to about 1:5, most preferably 1:1 ratio have been found to provide the greatest microbial blocking activity. In one preferred embodiment, the composition is an aqueous solution containing such a mixture of Im-LF and native LF. In some preferred embodiments, the composition contains a mixture of about 1% wt/vol Im-LF and about 1% wt/vol native lactoferrin.

Mixtures of Im-LF and native LF are formed by adding excess LF to the substrate. In a preferred aqueous dispersion embodiment, from about 0.001% wt/vol to about 2.5% wt/vol, preferably from about 0.5% wt/vol to about 2.0% wt/vol, most preferably about 1% wt/vol of LF is added to a dispersion containing 0.01% wt/vol galactose-rich polysaccharide or other substrate as described herein above.

If no native LF is present in the inventive composition (meaning that 100% of the LF is Im-LF), the apparent binding affinity of the Im-LF with a product (e.g., meat) or other biological surface will be lower than the apparent binding affinity of LF or a mixture of Im-LF and LF, thus, yielding relatively lesser retention of Im-LF on the surface over time after the composition is sprayed or otherwise applied. On the other hand, Im-LF, without added native LF, yields enhanced antimicrobial activity compared to LF or a mixture of Im-LF and LF. Thus, a mixture of Im-LF and native LF yields a comparatively higher apparent binding affinity and retention, but if too much native LF is added to the mixture, undesirable non-specific antimicrobial properties will become significant.

The inventive compositions comprise a defined dispersion. A "dispersion" includes an aqueous solution, an aqueous emulsion, a colloid, a suspension, a powder, or a granular solid that contains the Im-LF. A "defined dispersion" is dispersion made, blended, concocted, constructed, synthesized, or assembled of preselected ingredients or components, each in preselected amounts. Dispersion can be accomplished in various ways. A first way is that of a solution, most preferably an aqueous solution containing the Im-LF. A second way is that of an emulsion, i.e., a 2-phase system in which one liquid is dispersed in the form of small globules throughout another liquid that is immiscible with the first liquid. (Swinyard and Lowenthal, "Pharmaceutical Necessities" *REMINGTON'S PHARMACEUTICAL SCIENCES*, 17th ed., AR Gennaro (Ed), Philadelphia College of Pharmacy and Science, 1985 p. 1296). Aqueous emulsions containing a second hydrophobic liquid phase are preferred. A third way is that of a suspension of a solid phase containing the Im-LF, either dispersed within a liquid phase, such as a colloid suspension of Im-LF, or dispersed among other solids (e.g., microcrystalline suspension), the composition thus having the form of a powder or a granular solid. In various embodiments, such solid dispersions containing Im-LF can be applied to surfaces directly, for example by spraying or can be contained in pharmaceuticals such as tablets, capsules, ointments, or the like. Solid dispersions have obvious advantages with respect to storage and transport, and such solid dispersions containing Im-LF can later be suspended or dissolved in a liquid phase before use, as appropriate or convenient. Any of the solutions, emulsions or suspensions can be incorporated into capsules, or a microsphere or particle (coated or not) contained in a capsule.

In non-liquid dispersion embodiments (e.g., solid dispersions such as powders and granular dispersions), from about 0.001% wt Im-LF/total wt to about 2.5% wt Im-LF/total wt, preferably from about 0.5% wt Im-LF/total wt to about 2.0% wt Im-LF/total wt, most preferably about 1% wt Im-LF/total wt is added to a dispersion containing 0.01% wt Im-LF/total wt galactose-rich polysaccharide or other substrate as described herein above. Similar concentrations of native LF can be added to the non-liquid dispersion embodiments to form mixtures of Im-LF and native LF.

As well as an Im-LF, pharmaceutically acceptable formulations of the inventive compositions contain at least one pharmaceutically acceptable carrier. As used herein, "pharmaceutically acceptable carrier" encompasses any of the standard pharmaceutical carriers known to those of skill in the art. Pharmaceutically acceptable carriers include solvent(s), vehicle(s), adjuvant(s), excipient(s), binder(s), thickener(s), suspending agent(s), or filler substance(s) that are known to the skilled artisan suitable for administration to human and/or non-human vertebrates. For example, one useful carrier is a commercially available emulsion, Ensure®, but the inventive compositions are also dispersible in gravies, dressings, sauces or other comestible carriers. Other useful carriers include, but are not limited to, solid, semisolid or liquid glucose, lactose, sucrose, or polymeric substances like starch or dextran.

Useful carriers also include any emulsifier or suspending agent that is pharmaceutically acceptable, which is used as a vehicle for dispersion. Useful emulsifiers include monoglyceride compounds, diglyceride compounds, triglyceride compounds, glycerol, and phospholipids, such as phosphatidyl ethanolamine, phosphatidyl choline, or lecithin. Other useful carriers include gum acacia, agar, petrolatum, lanolin, dimethyl sulfoxide (DMSO), normal saline (NS), phosphate buffered saline (PBS), sodium alginate, bentonite, carbomer, carboxymethylcellulose, carrageenan, powdered cellulose, cholesterol, gelatin, hydroxyethyl cellulose, hydroxypropyl cellulose, hydroxypropyl methylcellulose, methylcellulose, octoxynol 9, oleyl alcohol, polyvinyl alcohol, povidone, propylene glycol monostearate, sodium lauryl sulfate, sorbitan esters, stearyl alcohol, tragacanth, xanthan gum, chondrus, glycerin, trolamine, avocado oil, almond oil, coconut oil, coconut butter, propylene glycol, ethyl alcohol, malt, and malt extract.

Some embodiments of the inventive compositions also include additional medicinal or nutritive additives in combination with Im-LF, to suit the more particular needs of the practitioner. These can include other useful antimicrobial agents, such as antibiotics, and/or probiotic agents, as described herein below.

In some embodiments, the Im-LF is added to the foodstuff as part of a comestible dispersion that can also include a suitable medium or carrier for convenient mixing or dissolving into a particular foodstuff or for applying to the surface of a foodstuff. Also, in some embodiments, the dispersion additionally contains a mixture of native LF and Im-LF. In such embodiments, the concentration of Im-LF/native-LF mixture in comestible formulations is typically from about 0.001% to 2.5% wt/vol, preferably about 0.5% to 2.0% wt/vol, most preferably about 1% wt/vol.

The dispersion is preferably one that will not interfere with the familiar flavor of the food of interest, such as are known by the artisan skilled in food processing techniques. For example, a comestible aqueous dispersion typically contains water. Suitable emulsifiers include mono-, di-, or triglyceride compounds, glycerol, phosphatidyl ethanolamine, phosphatidyl choline, or lecithin. A most preferred embodiment includes a mixture of mono- and diglyceride compounds, such as found in a commercially available mixture like GRUENAU Mono & Diglycerides, or C.G. 340-E (Bavaria Corporation, Altamonte Springs, Fla.), containing 35-45% monoglycerides.

Optionally, the aqueous dispersion contains other components as are known in the art for preserving or enhancing foodstuffs or food products, particularly for meat products, such as brines, starches (e.g., potato starch, corn starch, tapioca starch, or rice starch), maltodextrin, plasma or meat stock proteins, amino acids, protein or starch hydrolysates, antioxidants and/or flavorants. (E.g., C. L. Gilchrist, Method of processing meat, U.S. Pat. No. 5,714,188; P. A. Inklaar, Method of improving dehydrated raw animal meat, U.S. Pat. No. 3,681,095 and Method for improving the quality of meat-containing foods, U.S. Pat. No. 3,552,978; K. Nishimori and Y. Nakao, Method and composition for preventing discoloration of meat products, U.S. Pat. No. 4,590,079; J. H. Ernster, Hydrolyzed protein composition and process used in preparation thereof, U.S. Pat. No. 4,545,933; K. Tamaki et al., Low calorie meat products and a process for producing the products, U.S. Pat. No. 5,039,539).

A flavorant can be a natural extractive of a spice plant or herb, for example, rosemary, sage, basil, oregano or any other pleasant herbal or fruity flavorants or mixture of flavorants. Synthetic flavorants are also suitable. The flavorant can also have antimicrobial properties.

Typically, the concentration of Im-LF on a biological or product surface treated in accordance with the inventive methods is from about 0.0001 to about 10 mg/sq.inch.

In a preferred embodiment, the composition contains a buffer system including a combination of a physiologically acceptable acid, such as oxalic acid, ethylenediamine tetraacetic acid, carbonic acid (which can be added in aqueous form or by gassing an aqueous solution or emulsion with carbon dioxide), or citric acid, preferably citric acid; a physiologically acceptable base, preferably sodium bicarbonate potassium bicarbonate, sodium carbonate, or potassium carbonate; and a physiologically acceptable salt such as calcium chloride, potassium chloride or sodium chloride, preferably sodium chloride. The citrate and bicarbonate ratio in the buffer is significant for co-ordinated metal binding properties of LF, which play an important factor in enhancing the stasis effect and microbial blocking activity of the LF. The molar ranges of acid:base:salt is typically about 0.1 to 0.0001 M (acid): 1 to 0.001 M (base): 10 to 0.01 M (salt); with 0.01-0.001 M (acid): 0.1 to 0.01 M (base): 1 to 0.1 M(salt), preferred; and 0.001 M (acid): 0.01 M (base): 0.1 M(salt), most preferred. Examples of preferred embodiments are thusly buffered aqueous solutions, emulsions, colloids, or suspensions.

The preferred pH range for aqueous solutions containing Im-LF is about pH 4 to about pH 8, most preferably between about pH 5.5 to about pH 7.5. If a specific pH is desired for a specific application, then to acidify aqueous solutions, any food or pharmaceutical grade acid is employed (e.g., citric, lactic, phosphoric, or acetic acid), as appropriate. To make the dispersion more alkaline, a mono-, di-, or tri-basic phosphate salt is typically used.

For sterilizing the inventive compositions, for example aqueous solutions containing Im-LF, aseptic filtration is most preferred, but gamma irradiation is also useful. The inventive compositions are not autoclavable. However they can be pasteurized, which is useful, for example, in many food processing applications.

The inventive compositions include medicaments taken into the bodies of humans or non-human vertebrate animals, or applied topically thereto, by a delivery system. A medicament is a therapeutic agent or substance, such as a drug, medicine, irrigant, bandage, or other medical or dental device, that promotes recovery from injury or ailment or prevents or alleviates the symptoms of disease. The inventive medicaments of the invention, containing Im-LF, can be formulated for any suitable systemic or non-systemic delivery system, including delivery systems for oral, enteral, or parenteral delivery routes. Examples include tablets, troches, lozenges, aqueous or oily suspensions, dispersible powders or granules, emulsions, hard or soft capsules, syrups, beverages, elixirs or enteral formulas, lavage or enema solutions, adhesive patches, infusions, injectates, intravenous drips, inhalants, or implants. Dental irrigants, tooth pastes, tooth powders, and other dentifrices, cleansing or sanitizing agents for dentures (e.g., effective against *Candida albicans, Pseudomonas*, or streptococci), mouthwash orgargle solutions, chewing gums, shampoos, and sanitary wipes and gauze bandages (with or without adhesive) containing Im-LF, are additional useful delivery system formulations of the inventive compositions. Delivery systems also include topical creams, gels, suppositories, or ointments for non-systemic localized delivery or systemic delivery via the blood stream.

The inventive compositions containing Im-LF in suitable pharmaceutically acceptable formulations are useful for treating humans, including children and infants (i.e., pediatric uses), and non-human vertebrate animals. The inventive compositions are formulated for acceptable delivery to a human or non-human vertebrate gastrointestinal tract or other body site or tissue. Topical delivery to gastrointestinal mucosa and/or systemic delivery thereto are intended. Also included are pharmaceutically acceptable formulations intended for systemic or topical delivery to a non-gastrointestinal body site or tissue subject to microbial contamination.

Compositions intended for an oral delivery route may be prepared according to any method known to the art for the manufacture of pharmaceutical compositions. Compositions may also be coated by the techniques described in the U.S. Pat. Nos. 4,256,108; 4,160,452; and 4,265,874, to form osmotic therapeutic tablets for controlled release. Other techniques for controlled release compositions, such as those described in the U.S. Pat. Nos. 4,193,985; and 4,690,822; 4,572,833 can be used in the formulation of the inventive compositions. A most preferred embodiment of the pharmaceutical composition of the present invention is formulated for a non-systemic ingestive delivery system, such as, but not limited to a tablet, capsule, or caplet.

Preferably, the non-systemic ingestive delivery system comprises an enteric coating to prevent esophageal or gastric release of Im-LF. Such enteric-coated pharmaceuticals disintegrate after leaving the stomach, resulting in drug dispersion in the small intestine or colon where Im-LFs will act topically at the intestinal mucosa. As the skilled artisan will be aware, controlled release or enteric-coated drug delivery systems typically involve pH-sensitive, polymer-coated tablets, capsules, or caplets. A polymer coating can be selected that will direct release of a dispersion containing Im-LF to a particular region of the gastrointestinal tract. Such polymers include, but are not limited acrylic polymers such as Eudragit-L or Eudragit-S, and cellulosic polymers, such as ethylcellulose.

For example, amphionic ethylcellulose, dissolves at either acidic or basic pH to release the dispersion it contains. Other formulations of the inventive compositions include acrylic polymer coating(s) having various pH sensitivities. For example, the acrylic polymer coating Eudragit-S is degraded at above pH 7.0. Thus, it is carried to the portion of the gastrointestinal tract where intraluminal pH is elevated above 7.0, after passing through the far more acidic milieu of the stomach, and as a result, the dispersion containing Im-Lf is reliably released in the distal small intestine (ileum) and colon of a human patient. (M. J. Dew et al., *An oral preparation to release drug in the human colon*, Br. J. Clin. Pharmacol. 14:405-08 [1982]). Another example of a controlled release formulation of the inventive composition is a dispersion coated first with a semipermeable layer of ethylcellulose and second with an acrylic polymer, such as Eudragit-L, which is degraded at above pH 5.6 in the distal small intestine and colon to release and deliver the inventive composition there.

In addition, tablets, capsules, or caplets can be formulated in a multi-layer configuration for slow release over an extended period, as known in the art.

Systemic delivery systems that are contemplated by the present invention include, but are not limited to, ingestion, injection, or intravenous drip, most conventionally. Other useful systemic delivery systems are known and include, but are not limited to, implant; adhesive transdermal patches; topical creams, gels or ointments for transdermal delivery; transmucosal delivery matrices or suppositories or gels. It is contemplated that the compositions of the present invention are formulated to deliver an effective amount of Im-LF by these or any other pharmaceutically acceptable systemic delivery system.

A preferred embodiment of the compositions of the present invention employing a systemic delivery route is a topical cream, ointment or gel to be applied to the skin. In this embodiment, a composition of the present invention comprises Im-LF in a pharmaceutically acceptable delivery system comprising a permeation or penetration enhancer, such as polyethylene glycol monolaurate, dimethyl sulfoxide,-vinyl-2-pyrrolidone, N-(2-hydroxyethyl)-pyrrolidone, or 3-hydroxy-N-methyl-2-pyrrolidone. It is the permeation or penetration enhancer that distinguishes these compositions from other inventive topical creams, ointments, and gels formulated for non-systemic delivery. A variety of conventional thickeners often used in creams, ointments and gels, such as, but not limited to, alginate, xanthan gum, or petrolatum, may also be employed in various embodiments.

Another preferred embodiment of the compositions of the present invention is a formulation for systemic transmucosal delivery of Im-LF. A variety of pharmaceutically acceptable systems for transmucosal delivery of therapeutic agents are known in the art and are compatible with the practice of the present invention. (Heiber et al., Transmucosal delivery of macromolecular drugs, U.S. Pat. Nos. 5,346,701 and 5,516,523; Longenecker et al., Transmembrane formulations for drug administration, U.S. Pat. No. 4,994,439). Transmucosal delivery devices may be in free form, such as a cream, gel, or ointment, or may comprise a determinate form such as a tablet, patch, or troche. For example, delivery of Im-LF may be via a transmucosal delivery system comprising a laminated composite of, for example, an adhesive layer, a backing layer, a permeable membrane defining a reservoir containing Im-LF a peel seal disc underlying the membrane, one or more heat seals, and a removable release liner. (Ebert et al., Transdermal delivery system with adhesive overlay and peel seal disc, U.S. Pat. No. 5,662,925; Chang et al., Device for administering an active agent to the skin or mucosa, U.S. Pat. Nos. 4,849,224 and 4,983,395).

Alternatively, a tablet or patch for delivery through the oral mucosa can comprise an inner layer containing the therapeutic agent of choice, a permeation enhancer, such as a bile salt or fusidate, and a hydrophilic polymer, such as hydroxypropyl cellulose, hydroxypropyl methylcellulose, hydroxyethylcellulose, dextran, pectin, polyvinyl pyrrolidone, starch, gelatin, or any of a number of other polymers known to be useful for this purpose. This inner layer can have one surface adapted to contact and adhere to the moist mucosal tissue of the oral cavity and may have an opposing surface adhering to an overlying non-adhesive inert layer. Optionally, such a transmucosal delivery system can be in the form of a bilayer tablet, in which the inner layer also contains additional binding agents, flavoring agents, or fillers. Some useful systems employ a non-ionic detergent along with a permeation enhancer. These examples are merely illustrative of available transmucosal delivery technology and are not limiting of the present invention.

Another preferred embodiment of the compositions of the present invention is a gel formulated for systemic delivery of Im-LF via the rectal or vaginal mucosa, similar to gels commonly used for the delivery of various other therapeutic agents. Hydrogel matrices are known for this purpose. (Feijen, Biodegradable hydrogel matrices for the controlled release of pharmacologically active agents, U.S. Pat. No. 4,925,677). Such biodegradable gel matrices can be formed, for example, by cross-linking a proteinaceous component and a polysaccharide or mucopolysaccharide component, then loading with Im-LF to be delivered.

Another preferred embodiment of the compositions of the present invention is a formulation for the systemic delivery of Im-LF via a biodegradable matrix implanted within the body or under the skin of a human or non-human vertebrate. The implant matrix may be a hydrogel similar to those described above. Alternatively, it may be formed from a poly-alpha-amino acid component. (Sidman, Biodegradable, implantable drug delivery device, and process for preparing and using same, U.S. Pat. No. 4,351,337).

A preferred embodiment of the composition of the present invention employing a systemic delivery route is a transdermal delivery system of a kind known in the art for delivering various drugs. Transdermal delivery systems can be of any number of varieties known in the art. For example, delivery of Im-LF can be via a transdermal delivery system comprising a laminated composite of an adhesive layer, a backing layer, a permeable membrane defining a reservoir containing Im-LF, a peel seal disc underlying the membrane, one or more heat seals, and a removable release liner. (Ebert et al., Transdermal delivery system with adhesive overlay and peel seal disc, U.S. Pat. No. 5,662,925; Chang et al., Device for administering an active agent to the skin or mucosa, U.S. Pat. Nos. 4,849,224 and 4,983,395).

Alternatively, a transdermal delivery device can be a matrix type transdermal patch. (Chien et al., Transdermal estrogen/progestin dosage unit, system and process, U.S. Pat. Nos. 4,906,169 and 5,023,084; Cleary et al., Diffusion matrix for transdermal drug administration and transdermal drug delivery devices including same, U.S. Pat. No. 4,911,916; Teillaud et al., EVA-based transdermal matrix system for the administration of an estrogen and/or a progestogen, U.S. Pat. No. 5,605,702; Venkateshwaran et al., Transdermal drug delivery matrix for coadministering estradiol and another steroid, U.S. Pat. No. 5,783,208; Ebert et al., Methods for providing testosterone and optionally estrogen replacement therapy to women, U.S. Pat. No. 5,460,820). The matrix of the patch can comprise a basal support layer, such as an acrylic or ethylene/vinyl acetate copolymer or a polyurethane foam or cellulosic material, and an adhesive, such as, but not limited to, polysiloxane. In the compositions of the present invention, the polymer matrix also contains Im-LF, as described above, and optionally, a penetration-enhancing vehicle or carrier, such as N-vinyl-2-pyrrolidone, N-(2-hydroxyethyl)-pyrrolidone, or 3-hydroxy-N-methyl-2-pyrrolidone. The adhesive patch may be pressure-sensitive, to release the Im-LF across the skin of the patient when the patch matrix has been applied to the skin. The patch may optionally comprise an inert backing layer in addition to a matrix layer, or can comprise multiple dosage units or layers.

Another preferred embodiment of the compositions of the present invention, employing a pharmaceutically acceptable non-systemic delivery route, is a suppository or foam for delivery of a composition comprising Im-LF for delivery routes via urogenital structures, anus, or rectum. Once delivered, Im-LF of the present invention will act topically at the intestinal mucosa. Such suppository or foam delivery systems are known in the art. Together with Im-LF pharmaceutical formulation of the inventive compositions, such as a suppository, can employ a variety of conventional thickeners or suspenders, such as alginate, xanthan gum, lanolin, or petrolatum. Also contemplated are suppositories or foams comprising hydrophilic polymers, such as hydroxypropyl cellulose, hydroxypropyl methylcellulose, hydroxyethylcellulose, dextran, pectin, polyvinyl pyrrolidone, starch, gelatin, or any of a number of other polymers known to be useful for this purpose.

Another preferred embodiment of the compositions of the present invention is a gel for non-systemic delivery of a composition comprising Im-LF, similar to gels commonly used for the delivery of other chemotherapeutic agents. Hydrogel matrices are known for this purpose. (Feijen, Biodegradable hydrogel matrices for the controlled release of pharmacologically active agents, U.S. Pat. No. 4,925,677). Such biodegradable gel matrices may be formed, for example, by cross-linking a proteinaceous component and a polysaccharide or mucopolysaccharide component, then loading with Im-LF, for deliverability over an extended period. Another preferred delivery system comprises a lavage system, whereby a patient will ingest a large volume of an osmotically balanced flushing solution, containing Im-LF, or a conventional flushing solution in conjunction with another ingestible form of Im-LF antimicrobial agent. Such a lavage system can virtually eliminate harmful bacterial populations from the intestine. This may be especially desirable in refractory cases of bacterial overgrowth or in preparing a patient for abdominal surgery. Commercially available lavage or enema solutions, such as Go-lytely or fleet phosphosoda preparations can be used as carriers to formulate the inventive composition. A lavage or enema solution is optionally combined with one or more antibiotic(s) or other antimicrobial agent(s). (E.g., J. A. Vanderhoof et al., *Treatment strategies for small bowel bacterial overgrowth in short bowel syndrome*, J. Pediatr. Gastroenterol. Nutr. 27(2): 155-60 [1998])

Another preferred ingestive delivery system is especially, but not exclusively, useful for veterinary applications. In this embodiment a pharmaceutical preparation of the present invention is formulated and prepared to be ingested by an animal along with its food, as part of a pharmaceutically acceptable feed mixture. A pharmaceutically acceptable food additive or supplement for humans is also contemplated. For example, Im-LF-containing composition can be added to a foodstuff.

In some embodiments of the inventive methods, the Im-LF is delivered in conjunction with a probiotic agent, for example, an inoculum of a lactic acid bacterium or *bifidobacterium*. (A. S. Naidu et al., *Probiotic spectra of lactic acid bacteria*, Crit. Rev. Food Sci. Nutr. 39(1):13-126 [1999]; J. A. Vanderhoof et al. [1998]; G. W. Tannock, *Probiotic properties of lactic acid bacteria: plenty of scope for R & D*, Trends Biotechnol. 15(7):270-74 [1997]; S. Salminen et al., *Clinical uses of probiotics for stabilizing the gut mucosal barrier: successful strains and future challenges*, Antonie Van Leeuwenhoek 70(24):347-58 [1997]). The inoculum is delivered in a pharmaceutically acceptable ingestible formulation, such as in a capsule, or for some subjects, consuming a food supplemented with the inoculum is effective, for example a milk, yoghurt, cheese, meat or other fermentable food preparation. The inoculum of the probiotic agent is preferably, but not necessarily, included as a further component of an inventive Im-LF-containing composition.

Useful probiotic agents include bacteria of the genera *Bifidobacterium, Streptococcus, Pediococcus, Lactococcus,* or *Lactobacillus* species or strains, e.g., *Bifidobacterium bifidum, Bifidobacterium longum, Bifidobacterium animalis, Streptococcus lactis, Streptococcus cremoris, Streptococcus thermophilus, Pediococcus pentoseus, Lactococcus lactis, Lactobacillus acidophilus, Lactobacillus rhamnosus, Lactobacillus plantarum, Lactobacillus reuteri, Lactobacillus bulgaricus, Lactobacillus paracasei* (e.g., *L. paracasei* subsp. *paracasei*), or *Lactobacillus casei* (e.g., *L. casei* Shirota or L casei GG). (E.g., P. Kontula et al., *The effect of lactose derivatives on intestinal lactic acid bacteria*, J. Dairy Sci. 82(2):249-56 [1999]; M. Alander et al., *The effect of probiotic strains on the microbiota of the Simulator of the Human Intestinal Microbial Ecosystem (SHIME)*, Int. J. Food Microbiol. 46(1):71-79 [1999]; S. Spanhaak et al., *The effect of consumption of milk fermented by Lactobacillus casei strain Shirota on the intestinal microflora and immune parameters in humans*, Eur. J. Clin. Nutr. 52(12): 899-907 [1998]; W. P. Charteris et al., *Antibiotic susceptibility of potentially probiotic Lactobacillus species*, J. Food Prot. 61(12): 1636-43 [1998]; B. W. Wolf et al., *Safety and tolerance of Lactobacillus reuteri supplementation to a population infected with the human immunodeficiency virus*, Food Chem. Toxicol. 36(12): 1085-94 [1998]; G. Gardiner et al., *Development of a probiotic cheddar cheese containing human-derived Lactobacillus paracasei strains*, Appl. Environ. Microbiol. 64(6):2192-99 [1998]; T. Sameshima et al., *Effect of intestinal Lactobacillus starter cultures on the behaviour of Staphylococcus aureus in fermented sausage*, Int. J. Food Microbiol. 41(1):1-7 [1998]).

The inventive compositions and methods described herein are useful against a wide variety of bacteria, such as, but not limited to pathogenic and non-pathogenic strains of:

(A) Gram-negative facultative anaerobes of the enteric group, for example, *Escherichia coli; Helicobacter pylori; Salmonella* spp., including *Salmonella typhimurium, Salmonella typhi, Salmonella enteritidis Salmonella abony, Salmonella dublin, Salmonella hartford, Salmonella kentucky, Salmonella panama, Salmonella pullorum, Salmonella rostock, Salmonella thompson, Salmonella virschow; Enterobacter* spp., such as *Enterobacter aerogenes; Klebsiella pneumoniae; Shigella* spp., such as *Shigella dysenteriae* or *Shigella flexneri; Vibrio* spp., including *Vibrio cholerae; Yersinia enterocolitica* and *Yersinia pestis.*

(B) Gram-negative aerobic motile rods such as *Bordetella pertussis; Campylobacter jejuni;* and *Pseudomonas* spp., such as *Pseudomonas aeruginosa;*

(C) Gram-negative aerobic non-motile rods such as *Brucella* spp.; *Legionella pneumophila;* and *Francisella tularensis;*

(D) Gram-positive bacteria, including coccoid forms such as *Staphylococcus* spp., such as *Staphylococcus aureus, Staphylococcus epidermidis; Streptococcus* spp., such as, *Streptococcus pyogenes, Streptococcus pneumoniae, Streptococcus mutans, Streptocicccus sanguis; Pediococcus acne;* and bacillary forms such as *Bacillus* spp., including *Bacillus cereus, Bacillus anthracis, Bacillus pumilus, Bacillus subtilis; Clostridium* spp., including *Clostridium difficile, Clostridium tetani, Clostridium botulinum, Clostridium perfringens;* and *Listeria monocytogenes.*

(E) Periodontal pathogens such as *Actinobacillus actinomycetemcomitans, Porphyromonas gingivalis, Prevotella* spp., such as *Prevotella intenmedia.*

The inventive compositions and methods are also useful against fungal pathogens including dermatophytes, such as *Epidermophyton* spp.; *Microsporium* spp.; and *Trichophyton* spp.; systemic mycopathogens, such as *Blastomyces* spp.; *Coccidiodes* spp.; *Cryptococcus neoformans, Histoplasma* spp.; and yeasts, such as *Candida albicans.*

The inventive compositions and methods are also useful against protozoan parasites, such as *Entamoeba histolytica; Naegleria flowleri; Giardia lamblia; Leishmania* spp.; *Trichomonas vaginalis; Trypanosoma* spp.; *Plasmodium* spp.; and *Taxoplasma* spp.

The inventive compositions and methods are also useful against viral pathogens, including herpesviruses, such as HHV-6 and HHV-8, Cytomegalovirus (CMV), Epstein-Barr virus (EBV), Herpes Simplex viruses (HSV), varicella viruses; picoma viruses such as Coxsackie viruses, Hepatitis A virus; rhinoviruses; reoviruses, such as the rotaviruses; influenza and parainfluenza viruses.

The inventive compositions and methods can, optionally, be used in combination with other known antimicrobial agents, including lacto-antimicrobials, such as lactoperoxidase, lactoglobulins, lactooligosaccharides, lactolipids, lactoglobulins; ovo-antimicrobials, such as ovotransferrin, lysozyme, avidin, ovoglobulin, riboflavin-binding protein, ovomucoid protease inhibitor; phyto-antimicrobials, such as thiosulfinates, glucosinolates, flavonoids, essential oils, phenolates, catechins; bacteriocins, such as nisin, pediocin, reuterin, or sakacin; acid-antimicrobials, such as lactic acid, acetic acid, citric acid, sorbic acids; ionic antimicrobials, such as polyphosphates, nitrites; sulfur-compounds; chlorocides; ozone; or a natural, synthetic, or an semi-synthetic antibiotic agent, such as neomycin, metronidazole, teicoplanin, vancomycin, ciprofloxacin, doxycycline, tetracycline, augmentin, erythromycin, chloramphenicol, cephalexin (e.g., Keflex), penicillin, ampicillin, kanamycin, rifamycin, rifaximin, rifampin, clindamycin, trimethoprim, a 4-amino salicylate compound, a 5-aminosalicylate compound, a sulfonamide compound, a betalactam compound, an aminoglycoside compound, a macrolide compound, or a quinolone compound.

Moreover, the inventive compositions can act synergistically to potentiate some antibiotic agents, including betalactams, chloramphenicol, aminoglycosides, clindamycin, vancomycin, sulfonamides, trimethoprim, rifampin, tetracyclines, metronidazole, quinolones, erythromycin and other macrolides.

The present invention includes a method of preventing or inhibiting the growth and/or adhesion of a microbe in or on a vertebrate subject, including a human subject. The human subject can be an infant, child, or adult. The method is also useful for veterinary purposes. The present method is useful for treating a non-human vertebrate including, but not limited to, a wild, exotic, domestic, or farm animal. The method is useful for treating a mammal such as a non-human primate, mouse, rat, rabbit, gerbil, hamster, canine, feline, ovine, bovine, swine, pachyderm, equine, or marine mammal. Also, the method is useful for treating a bird (i.e., avian or poultry), such as a chicken, duck, goose, turkey, ostrich, emu, dove, pigeon, quail, pheasant, peafowl, or guinea fowl. Egg laying hens and other table egg layers can also be treated in accordance with the method. Typically, the subject requires treatment for a microbial infection or overgrowth by a microbe, but prophylactic treatment is also encompassed by the method.

The inventive compositions and method are useful in reducing microbial infection, adhesion, and/or contamination on biological surfaces, in biological fluids, and interspaces within biological tissues. Biological surfaces include cell surfaces, membranes, mucosa, epithelia, lumenal surfaces, eggshell surfaces, or skin (including, hair, fur, nails, claws, or feathers) surfaces, of a human or non-human vertebrate, including vascular epithelium, oral epithelium, vaginal epithelium, cervical epithelium, uterine epithelium, intestinal epithelium, bronchial epithelium, esophageal epithelium, pleura, pericardium, peritoneum, mesothelium, or any other surface at any body site, limb, organ and/or tissue. Included are surfaces of the organs of the gastrointestinal tract, which include the esophagus, stomach, large intestine, small intestine, or rectum. The skilled artisan will be aware that in a non-human vertebrate the digestive tract may include a rumen, crop, gullet, cecum, or other specialized organ as pertains to a particular vertebrate species. Other body sites, limbs, organs and/or tissues include, but are not limited to, skin, heart, lung, blood, kidney, bladder, liver, brain, sensory organs such as eyes or ears, arms, legs, feet, digits, sexual organs (e.g., testis, penis, prostate, ovary, uterus, breast, udder), trunk, head, neck, fin, flipper, or tail. Biological surfaces and fluids can be in vivo, i.e., within a vertebrate organism, or in vitro, for example surfaces of cultured cells or tissues, or fluid specimens.

Biological fluids subject to microbial contamination or infection include blood, lymph, urine, semen, prostatic fluid, saliva, gastricjuice, mucus, synovial fluid, pleural exudate, peritoneal exudate, pericardial exudate, or cerebro-spinal fluid. Culture media are also encompassed by "biological fluids".

The inventive method is particularly useful in preserving biological fluid specimens, for example, semen specimens (e.g., used in artificial insemination), or as an antimicrobial supplement in culture media. Inventive aqueous solutions containing Im-LF are preferred for such applications.

Administering the inventive Im-LF-containing composition, an a pharmaceutically acceptable formulation, to a human or non-human vertebrate subject is by any pharmaceutically acceptable delivery route. "Administering" includes giving, providing, feeding or force-feeding, dispensing, injecting, infusing, inserting, prescribing, furnishing, treating with, taking, swallowing, eating, spreading, or applying a composition of the present invention.

In one embodiment, the pharmaceutically acceptable composition is administered by a non-systemic delivery route to the site of microbial infection or overgrowth, which delivery route is not primarily by way of the blood stream of a human or non-human vertebrate.

Some non-systemic delivery routes and pharmaceutically acceptable non-systemic delivery systems that could be employed by one of skill in the art in practicing the methods and compositions of the present invention are now exemplified. The following are presented merely to illustrate and in no way to limit the possible delivery means contemplated.

For gastrointestinal bacterial infection or bacterial overgrowth, suitable non-systemic delivery routes include, but are not limited to, an ingestive delivery route or a colonic delivery route. A most preferred delivery route is an ingestive delivery route, whereby the antimicrobial agent enters the gastrointestinal or digestive tract by way of voluntary or forced ingestion through the mouth.

Another non-systemic delivery route is useful for non-gastrointestinal infections, particularly infections of the skin or externally accessible wounds, lesions, or sites of infection or microbial contamination; this delivery route is topical application to the affected area of an antimicrobial cream, gel, vaginal suppository, or ointment.

For some applications, a preferred embodiment of the method of preventing or inhibiting the growth and/or adhesion of a microbe in or on a human or non-human vertebrate subject involves a systemic delivery route, i.e., a route whereby delivery of Im-LF to the site of infection or bacterial growth is primarily via the blood stream. Entry of Im-LF into the blood stream of a human or non-human vertebrate patient can occur by any route, system, device, method or mechanism, including those described herein. For the purposes of the present invention, a systemic delivery route can also include delivery through the skin, mucosa or epithelium of the mouth including the sublingual epithelium, the rectum, or the vaginal epithelium. This embodiment can be used to inhibit microbial growth in any body site or tissue, including the gastrointestinal tract. A systemic delivery route is also particularly, but not exclusively useful for gastrointestinally infected patients who are unable to effectively ingest a non-systemic formulation of the composition of the present invention due to persistent nausea, difficulty in swallowing, or other ingestion-preventing conditions, or who, due to resection or other condition of the bowel cannot accept a colonic delivery system.

Alternatively, a systemic delivery route can be employed to deliver Im-LF to body sites, limbs, organs and/or tissues other than those of the gastrointestinal tract, as described above. Applications can include but are not limited to treating or preventing infections, including clostridial infections, at any body site or tissue of a vertebrate. Such clostridial infections include, but are not limited to, gangrene or tetanus, caused, respectively, by *Clostridium perfringens* and *Clostridium tetani*, when these species grow in wounds and damaged tissues with low oxygen tension.

Some embodiments of the method further comprise administering an antimicrobial agent, other than Im-LF, such as an antibiotic agent or probiotic agent in conjunction with the Im-LF. Administering "in conjunction with" means that the antimicrobial or probiotic agent is co-administered simultaneously with the Im-LF, either in a single inventive composition or in separate compositions. Alternatively, administering "in conjunction with" means that administration of the antimicrobial or probiotic agent is part of the same course of treatment as the Im-LF, directed at a single contemporaneous infection, overgrowth, or disease condition. Useful antimicrobial and probiotic agents, in accordance with the method, include those described herein above.

An amount of Im-LF effective to inhibit the growth of a microbial species is such amount as sufficient to prevent or reduce cellular proliferation of a bacterial, fungal, or protozoan species, by either killing cells or by preventing or slowing cellular growth or reproduction, compared to the rate of growth or reproduction in the absence of Im-LF. Alternatively, the amount effective to inhibit the growth of a viral species is such amount as sufficient to prevent or reduce the rate of replication of virions, compared to the rate in the absence of Im-LF.

The effective amount for each human or non-human vertebrate subject will depend upon the size and physiologic reactions of the subject to whom or to which the pharmaceutical preparations of the present invention are administered. And these reactions and the antimicrobial activity of the administered amount can be monitored by the prescribing physician or veterinarian. The pharmaceutically acceptable compositions of the present invention can be formulated and manufactured at more than one concentration, such that modular incremental amounts of Im-LF are easily administered.

A minimum effective amount is as little as between about 5 and about 15 mg of Im-LF per day. Effective amounts of Im-LF at about 15 to about 150 mg per day, and about 150 to about 250 mg per day are sufficient for smaller human adults, children, and smaller non-human vertebrates, such as rodents, canines, chickens and turkeys. A higher effective amount for an adult human is about 250-6500 mg of Im-LF per day. Pediatric amounts are typically 10-20% of effective amounts for adult humans. Higher effective amounts, from about 1,000 mg/day, up to about 6,500 mg/kg body mass per day can be used for large non-human vertebrates, for example, for sheep and larger animals such as cattle, horses, and elephants. The foregoing are merely illustrative of the effective amounts and possible dosage units that can be employed in the pharmaceutical compositions of the present invention, and smaller or larger dosage units than these are also contemplated. Larger dosage units are especially useful for large non-human vertebrates, such as, but not limited to, bovine animals, horses, pachyderms, or large marine mammals; smaller dosage units are especially useful for pediatric application and for small vertebrates, such as, but not limited to, mice or chickens.

Useful applications of the inventive method include but are not limited to treating or preventing clostridial infections at any body site or tissue of a vertebrate. Such clostridial infections include, but are not limited to, gangrene or tetanus, caused, respectively, by *Clostridium perfringens* and *Clostridium tetani*, when these species grow in wounds and damaged tissues with low oxygen tension. The method is also useful to treat enteritis necroticans.

Other applications of the inventive method include treatment or prevention of viral diarrhea (e.g., caused by Rotavirus); bacterial gastroenteritis (e.g., caused by *E. coli*, salmonellosis, shigellosis, campylobacteriosis, or *Aeromonas*); parasital dysentry (e.g., Amebiasis, Giardiasis); Traveller's diarrhea or infantile diarrhea (e.g., caused by *E. coli* or Rotavirus); gastric ulcers (e.g., caused by *Helicobacter pylori*); food-borne infections and intoxications (e.g., caused by staphylococcal enterotoxicosis, Salmonellosis, Shigellosis, Listeriosis, *E. coli* enterotoxicosis and HUS, or *Bacillus cereus*); mucosal infections; urogenital tract infections (e.g., caused by P fimbriated *E. coli*, Genital Herpes, or Trichomonas vaginalis); throat infections or pharyngitis (e.g., caused by Group A streptococci); eye infections or conjunctivitis (e.g., caused by *Pseudomonas* spp. or viruses). Other applications include prevention or treatment of skin infections, such as pyogenic skin infections, scalp infections (e.g., dandruff), or acne. Oral hygiene applications include the prevention or treatment of oral infections, plaque (e.g., caused by *Streptococcus mutans*), and periodontal diseases (e.g., caused by *Porphyromonas gingivalis, Prevotella internedia*, or *Actinobacillus*).

Immunocompromised patients, especially, can benefit from treatment with the inventive compositions and method, for example, in post-traumatic or post-operative wound care; burn care; treatment or prevention of toxic shock; treatment or prevention of infections associated with the use of biomedical devices, such as intravenous and other catheters, stents, syringes, internal prostheses and implants, or continuous ambulatory peritoneal dialysis (CAPD) devices; or in cases of neutropenia or AIDS.

Antimicrobial activity by Im-LF against a specific bacterial species of interest is determined by routine means well known to the skilled practitioner. For example, a "lawn" of a bacterial species can be plated on an appropriate solid medium, and zones of growth inhibition around sterile cellulose disks impregnated with an Im-LF of interest can be measured. Similarly, inhibition assays in liquid media are also routinely accomplished.

Inhibition of bacterial growth in a gastrointestinal tract is measured by conventional means well known to the skilled artisan. For example, many facultative anaerobes or fermentative bacterial species found in the gastrointestinal tract produce detectable quantities of hydrogen or methane gas in the presence of certain sugars, which gases enter the blood stream of the host and are gradually exhaled. This is the basis for intestinal bacterial growth detection means, such as, but not limited to, the lactulose, glucose, xylose, or lactose breath hydrogen tests. (E.g., P. Kerlin and L. Wong, Breath hydrogen testing in bacterial overgrowth of the small intestine, Gastroenterol. 95(4):982-88 [1988]; A. Strocchi et al., *Detection of malabsorption of low doses of carbohydrate: accuracy of various breath $H_2$ criteria*, Gastroenterol. 105(5): 1404-1410 [1993]). Typically, after an overnight fast, the patient swallows a controlled quantity of a sugar substrate (e.g., lactulose, glucose, xylose, or lactose) and breath samples are taken at frequent time intervals, typically every 10 to 15 minutes for a two- to four-hour period. Samples are analyzed by gas chromatography or by other suitable techniques, singly or in combination. A variable fraction of the population fails to exhale appreciable hydrogen gas during intestinal fermentation of lactulose; the intestinal microflora of these individuals instead produce more methane. (G. Corazza et al., *Prevalence and consistency of low breath $H_2$ excretion following lactulose ingestion. Possible implicationsfor the clinical use of the $H_2$ breath test*, Dig. Dis. Sci. 38(11):2010-16 [1993]; S. M. Riordan et al., *The lactulose breath hydrogen test and small intestinal bacterial overgrowth*, Am. J. Gastroenterol. 91(9); 1795-1803 [1996]). Consequently, in the event of an initial negative result for breath hydrogen, or as a precaution, methane and/or carbon dioxide contents in each breath sample are optionally measured, as well as hydrogen, or a substrate other than lactulose is optionally used.

Alternatively, bacterial growth detection is by gas chromatography with mass spectrometry and/or radiation detection to measure breath emissions of isotope-labeled carbon dioxide, methane, or hydrogen, after administering an isotope-labeled substrate that is metabolizable by gastrointestinal bacteria but poorly digestible by the human or non-human vertebrate host, such as lactulose, xylose, mannitol, or urea. (E.g., G. R. Swart and J. W. van den Berg, $^{13}C$ *breath test in gastrointestinal practice*, Scand. J. Gastroenterol. [Suppl.] 225:13-18 [1998]; S. F. Dellert et al., *The 13C-xylose breath test for the diagnosis of small bowel bacterial overgrowth in children*, J. Pediatr. Gastroenterol. Nutr. 25(2):153-58 [1997]; C. E. King and P. P. Toskes, *Breath tests in the diagnosis of small intestinal bacterial overgrowth*, Crit. Rev. Lab. Sci. 21 (3): 269-81 [1984]; C. S. Chang et al., *Increased accuracy of the carbon-14 D-xylose breath test in detecting small-intestinal bacterial overgrowth by correction with the gastric emptying rate*, Eur. J. Nucl. Med. 22(10):1118-22 [1995]; A. Schneider et al., *Value of the $^{14}C$-D-xylose breath test in patients with intestinal bacterial overgrowth*, Digestion 32(2):86-91 [1985]; See, also, G. Mastropaolo and W. D. Rees, *Evaluation of the hydrogen breath test in man: definition and elimination of the early hydrogen peak*, Gut 28(6):721-25 [1987]). A poorly digestible substrate is one for which there is a relative or absolute lack of capacity in the host for absorption thereof or for enzymatic degradation or catabolism thereof.

Suitable isotopic labels include $^{13}C$ or $^{14}C$. For measuring methane or carbon dioxide, suitable isotopic labels can also include $^2H$ and $^3H$ or $^{17}O$ and $^{18}O$, as long as the substrate is synthesized with the isotopic label placed in a metabolically suitable location in the structure of the substrate, i.e., a location where enzymatic biodegradation by intestinal microflora results in the isotopic label being sequestered in the gaseous product. If the isotopic label selected is a radioisotope, such as $^{14}C$, $^{13}H$, or $^{15}O$, breath samples can be analyzed by gas chromatography with suitable radiation detection means.

Another method of detecting small intestinal bacterial overgrowth is by endoscopic visual inspection of the wall of the duodenum, jejunum, and/or ileum.

Direct gastrointestinal sampling or biopsy from any body site, limb, organ and/or tissue can also be used to measure the inhibition of microbial growth in a gastrointestinal tract or other body site, limb, organ and/or tissue. As the skilled artisan is aware, direct sampling at time intervals provides information about the growth inhibition of specific bacterial species of interest, to which breath testing is not well-suited. Samples are diluted and bacterial numbers can be assessed by conventional microbiological means, such as microscopy, culturing, and/or cell numeration techniques, including colony plating or Most Probable Number (MPN) techniques, or direct counting of bacterial cells. For direct bacterial cell counts, cells can optionally be labeled with specific markers, and counts can be accomplished manually or by devices such as fluorescence-activated cell sorting (FACS).

Alternatively, evidence of inhibition of bacterial growth can be inferred by the practitioner treating a bacterial infection or intestinal bacterial overgrowth in a human or non-human vertebrate subject with observation of an improvement in various infection- or overgrowth-related symptoms in response to the administration of a composition of the present invention.

The preceding are merely illustrative and non-exhaustive examples of techniques for detecting microbial infection or overgrowth.

The inventive compositions are especially effective in treating food-borne pathogens, food-borne radiation-resistant bacteria, and food spoilage microorganisms. For example, the inventive compositions and any of the inventive methods described herein are of use in preventing, reducing, and/or inhibiting microbial growth or contamination by a wide variety of microbes, including enterotoxigenic *Escherichia coli*, enteropathogenic *Escherichia coli*, *Shigella dysenteriae*, *Shigella flexneri*, *Salmonella typhimurium*, *Salmonella abony*, *Salmonella dublin*, *Salmonella hartford*, *Salmonella kentucky*, *Salmonella panama*, *Salmonella pullorum*, *Salmonella rostock*, *Salmonella thompson*, *Salmonella virschow*, *Campylobacter jejuni*, *Aeromonas hydrophila*, *Staphylococcus aureus*, *Staphylococcus hyicus*, *Staphylococcus epidermidis*, *Staphylococcus hominis*, *Staphylococcus warneri*, *Staphylococcus xylosus*, *Staphylococcus chromogenes*, *Bacillus cereus*, *Bacillus subtilis*, *Candida albicans*, and such radiation-resistant bacteria as: *Brochothrix thermospacta*, *Bacillus pumilus*, *Enterococcus faecium*, *Deinococcus radiopugnans*, *Deinococcus radiodurans*, *Deinobacter grandis*, *Acinetobacter radioresistens*, *Methylobacterium radiotolerans*, as well as other kinds of bacteria described herein above. In particular, microbial contamination by verotoxic *Escherichia coli*, including serotype O157:H7, can be prevented by the inventive technology.

The Im-LF of the inventive compositions is useful with any product prone to microbial contamination or proliferation. Thus, the present invention includes a method for inhibiting the growth and/or adhesion of a microbial species in a foodstuff that is useful for treating a composition subject to contamination, which is a foodstuff or food product, and also includes inventive foodstuffs or food products, particularly meat products, treated by the inventive method. A foodstuff for purposes of the present invention is any food or beverage that can be ingested. Bacterial growth in foodstuff, if uninhibited, can result in the release of bacterial exotoxins that can cause illness or death in a human or non-human vertebrate that consumes the foodstuff. The present method and foodstuffs are particularly useful in preventing clostridial food poisoning, for example, by *Clostridium perfringens*, or by *Clostridium botulinum*, the exotoxins of which cause botulism.

The inventive method employs a comestible formulation of the inventive composition containing Im-LF, which composition is added to the foodstuff. Any foodstuff can be treated using the present method, but foods for which the present method is especially useful include non-acidic foods, such as mayonnaise or other egg products, potato products, and other vegetable or meat products. Representative products include processed and unprocessed foodstuffs for human or for animal consumption.

For example, foodstuffs or food products include any suitable meat or meat product derived from, but not limited to, pork, beef, veal, lamb, sheep, goat, bison, elk, deer, antelope, horse, dog, poultry (e.g., such as chicken, turkey, duck, goose, guinea fowl, ostrich, quail, dove, pigeon, emu, pea hen), or the meat of any other mammalian or bird (avian) species. A "beef product" contains the meat of an adult mammal of the subfamily Bovinae, including cattle, buffalo, bison, and kudus. A "pork product" contains the meat of a pig. A "poultry product" contains the meat of a bird, such as a chicken, duck, goose, turkey, ostrich, emu, dove, pigeon, quail, pheasant, peafowl, or guinea fowl. "Meat" includes whole or ground muscle or organ (e.g. liver).

The inventive meat products include, but are not limited to, primal, subprimal, or case-ready cuts, sliced cuts of meat, with or without bone, and ground meat. Primals are the initial divisions of the animal carcass after slaughter, for example, major wholesale cuts such as the shoulder, belly, loin, ham, or bone-in-loin. Subprimals are subdivisions of primal cuts, such as tender loins or back ribs. Case-ready meat products are smaller subdivisions of subprimal cuts, such as chops, steaks, or ground meat products, such as sausages, salamis, hotdogs and the like, or cold cuts, such as processed deli meats.

The inventive meat product is typically a packaged meat product treated in accordance with the present method. Packaging may be by any conventional meat packaging means, including containing the meat product with a tray, a transparent film, such as shrink-wrap or Saran, or with a paper, including unwaxed or waxed paper, or wrapping, bagging, boxing, canning or jarring by any means suitable for a meat product.

Foodstuffs and food products also include the surfaces and/or flesh of marine or freshwater aquatic organisms, such as various fishes (e.g., tuna, salmon, halibut, cod, shark, swordfish, bass, herring, sardines, trout, carp, whitefish, and perch), mollusks (clams, scallops, oysters, mussels, snails, octopus, and squid), or crustaceans (e.g., crabs, shrimps, lobsters, and crayfish). Surfaces can include surfaces of edible parts or exposed inedible parts that are subject to contamination, such as shells, cuttlebones, or carapaces. Also included among foodstuffs or food products are vegetable foodstuffs and food products, which can include any edible fruits, seeds, nuts, roots, tubers, bulbs, stems, leaves, flower parts, blades, stipes, holdfasts, or sporangia of terrestrial or aquatic plants or algae.

The Im-LF-containing composition is applied by any suitable method. Representative methods include spraying the product or washing the product during various processing steps, or coating the final product by electrostatic spray dispersion, with an aqueous suspension, emulsion, or solution, or dehydrated powder form containing the Im-LF.

The Im-LF-containing composition is applied at any time during the preparation of the product to be treated. For example, when the product is a meat, the Im-LF can be applied during slaughter or during the carcass wash or, if the meat product is a ground meat product, during meat grinding or homogenization. After application, the concentration of Im-LF on the food surface typically ranges from 0.0001 to 10 mg/sq. inch of food surface, more preferably 0.01 to 1 mg/sq. inch of food surface, most preferably 0.25 mg/sq. inch of food surface.

For treating meat products or other foodstuffs that are preferably stored and transported at refrigerated temperatures, the components of an aqueous dispersion, preferably in the form of a solution or emulsion, are mixed, then the dispersion is chilled, preferably to 32-36° F., most preferably to 32-33° F., before applying it to the foodstuff. The chilled dispersion is applied to the meat or other foodstuff.

The aqueous dispersion can be applied externally to the meat or other foodstuff to form a coating on its surface by spraying, brushing, or soaking it with the solution or emulsion.

Alternatively, in some embodiments of the inventive meat product, the aqueous dispersion is applied internally so that it penetrates the surface of the flesh and/or bone. One way this is accomplished is by injecting the solution into the meat. Alternatively, the meat is soaked in the solution for a period ranging from two hours up to two days. This provides lesser penetration of solution than injection. However, by massaging or tumbling the meat while it is being soaked, greater penetration of solution is achieved, and shorter soaking times are required, for example 30 to 60 minutes. The degree of penetration by the solution depends on the speed (rpm) of massaging or tumbling that is employed, soak time, the specific formulation of the aqueous solution, and whether vacuum is applied during massaging or tumbling. Typically, good results are obtained using 30 minutes of massaging or tumbling with an applied vacuum, followed by release of vacuum, and then a second 30 minute period of tumbling with vacuum.

In some embodiments of the present invention, an Im-LF-containing coating is applied as a fine spray to form a film on the interior surface of casings before the casings are stuffed with a batter for making sausages, salamis, hot dogs or the like. For example, a suitable coating formulation is made by combining 1% Im-LF immobilized on GRP combined with a film-forming agent such as carrageenan, gelatin or collagen (type-I and type-II). The microbial blocking activity is retained and works to prevent microbial contamination of the encased food product.

After treatment in accordance with the present method, the treated meat product or other foodstuff is optionally packaged. Regardless of packaging, the treated meat product is most preferably stored under refrigerated conditions until final purchase by the consumer. A meat product is typically stored at a temperature between 29-40° F., preferably between 29-38° F., and most preferably at 29-34° F. Alternatively, the treated meat product is stored frozen.

Optionally, the packaged meat product can be stored and transported to market under a controlled gas mixture to preserve product color or other consumer desirability factors, as is known in the art. (E.g., C. S. Cheng, Process for prepacking fresh meat, U.S. Pat. No. 4,683,139; Hormel Foods Corporation, Chemical treatment and packaging process to improve the appearance and shelf life of fresh pork, U.S. Pat. No. 5,780,085).

The Im-LF in accordance with the invention is also useful in coatings or meat packaging materials. In some embodiments, 2% Im-LF is applied to wax-coated wrappings, cellulosic or polyethylene liners used as packing materials in meat industry. The coating is stable with full retention of its microbial blocking activity.

This method also is intended for bacteriostatic food packaging or handling and relies on the antimicrobial properties of Im-LF, in accordance with the present invention. The present method involves treating a food-contacting surface of a material that is pharmaceutically acceptable for food packaging or food handling purposes, with an Im-LF in an amount effective to inhibit the growth of a microbial species on a food contacting the surface.

Acceptable materials for food packaging or handling, in accordance with the invention, include, but are not limited to, paper, wood, cardboard, or other cellulosic polymers, including transparent and non-transparent cellulosic polymers, to which LF can be attached by its N-terminal moiety.

A food-contacting surface of a suitable polymeric material is treated with lactoferrin by enmeshing, implanting, or impregnating the compound within the polymeric material, by means known to the artisan skilled in food packaging and handling materials. The treated food-contacting surface has an amount of Im-LF between about 0.0001 to about 10 mg/square inch of food-contacting surface, more preferably about 0.01 to about 1 mg/sq. inch. This is sufficient concentration to inhibit the growth of a food-poisoning or botulism-causing bacterial species.

Alternatively, a suitable polymeric material is treated with Im-LF by covalent linkage, such as by conjugation of the Im-LF to the polymeric material through, for example, diazo bonds or amide bonds.

Alternatively, a polymeric or non-polymeric material is treated with Im-LF by coating the material with a coating formulation suitable for a desired coating means, such as, but not limited to, dipping, spraying or brushing onto a surface intended for food contact. A suitable coating formulation contains, in addition to Im-LF, an appropriate carrier(s), which carriers are known in the art. For example, the skilled practitioner can employ as a carrier a non-toxic polymeric resin, additionally containing an effective amount of Im-LF, which resin can be used to coat the food-contacting surface of the material, hardening in place upon it.

Direct sampling is conventionally used to measure bacterial numbers foodstuffs, including meat and meat products. Samples can be macerated and diluted and bacterial numbers can be assessed by conventional microbiological means such as, but not limited to colony plating or Most Probable Number (MPN) techniques, or direct counting of bacterial cells. For direct bacterial cell counts, cells can optionally be labeled with specific markers, and counts can be accomplished manually or by well-known devices such as fluorescence-activated cell sorting (FACS).

A hygienic condition is maintained in accordance with the present invention through the inhibition of microbial growth on meat products and other foodstuffs treated thereby, based on a suitable hygienic standard as defined in the art.

The present invention is also related to food containers and food-handling implements for holding a foodstuff, which includes containing, packaging, covering, storing, displaying, processing, cutting, chopping, impaling, kneading, manipulating or otherwise handling the foodstuff, such that a surface of the food container or implement comes in contact with the foodstuff.

The present food containers and food-handling implements comprise a material suitable for contact with food and have a food-contacting surface treated with Im-LF, as described above, in an amount effective to inhibit the growth and/or adhesion of a bacterial or other microbial species thereon. An effective amount is between about 0.0001 to about 10 mg/square inch of said food-contacting surface, more preferably about 0.01 to about 1 mg/sq. inch. The containers and implements are in any suitable disposable (i.e., single-use) or non-disposable (i.e., multi-use) configuration capable of holding a foodstuff. These configurations include, but are not limited to, shear wraps, sheets, papers, waxed papers, bags, cartons, trays, plates, bowls, covered and uncovered storage vessels, serving dishes, cups, cans, jars, bottles, or any other suitable container configuration for a particular foodstuff. Additional configurations especially useful for food handling purposes include, but are not limited to, gloves or mitts; utensils such as forks, spoons, knives, slicers, processors, juicers, grinders, chippers, hooks, presses, screws, openers, cutters, peelers, tongs, ladles, scoops, cups, chutes or spatulas; and cutting boards, kneading boards, mixing bowls, drying or cooling racks, or shelves.

The inventive containers, and implements are especially useful in inhibiting the growth and/or adhesion of food-poisoning bacterial species, such as enterotoxigenic *Escherichia coli, Salmonella* spp., or *Shigella* spp., or species that can release pathogenic exotoxins, such as, but not limited to, *Clostridium perfringens*, or *Clostridium botulinum*, the exotoxins of which cause botulism. They are especially, but not exclusively, useful in commercial and institutional food preparation contexts where food is handled and packaged in bulk, such as, but not limited to, food processing factories, canning plants, slaughterhouses, restaurants, cafeterias, salad bars, grocery outlets, and hospitals. The present method, containers and implements are useful for any kinds of foodstuff. They are particularly useful in situations where food is processed, packaged, stored, or displayed at a temperature, at or above room temperature, but insufficiently hot to kill bacterial cells and spores, for example, when food is kept under a warming light. But the present method, containers and implements are also useful in the home kitchen.

The present invention is also related to antimicrobial cleansers, polishes, paints, sprays, soaps, or detergents formulated for application to surfaces to inhibit the growth of a microbial species thereon. These surfaces include, but are not limited to surfaces, such as, countertops, desks, chairs, laboratory benches, tables, floors, bed stands, tools or equipment, doorknobs, and windows. The present cleansers, polishes, paints, sprays, soaps, or detergents contain a Im-LF that provides a bacteriostatic property. The cleansers, polishes, paints, sprays, soaps, or detergents can optionally contain suitable solvent(s), carrier(s), thickeners, pigments, fragrances, deodorizers, emulsifiers, surfactants, wetting agents, waxes, or oils. A preferred embodiment is a formulation for external use as a pharmaceutically acceptable skin cleanser, particularly for the surfaces of human hands.

In the present cleansers, polishes, paints, sprays, soaps, and detergents, the concentration of the Im-LF is, preferably, from about 0.001% wt/vol to about 2.5% wt/vol, more preferably from about 0.5% wt/vol to about 2.0% wt/vol.

The present cleansers, polishes, paints, sprays, soaps, and detergents are useful in homes and institutions, particularly but not exclusively in hospital settings for the prevention of nosocomial infections.

The compositions and methods of the present invention provide a much needed addition to the antimicrobial armamentarium against microbial contamination, infection adhesion, and/or overgrowths, especially by enteric and clostridial bacterial species that affect great numbers of humans and animals worldwide.

The foregoing applications for the methods and compositions of the present invention are illustrative and by no means exhaustive. The invention will now be described in greater detail by reference to the following non-limiting examples. All weights are based on percent weight/volume unless otherwise clearly indicated.

Example 1

An antimicrobial assay was performed using LF and Im-LF to demonstrate their inhibitory effects on the growth of *E. coli* serotype O157:H7 (strain ATCC43895). The *E. coli* was isolated from raw hamburger meat implicated in hemorrhagic colitis outbreak and known to produce shiga-like toxins I and II.

Preparation of Galactose-Rich Polysaccharide

A biologically active substrate containing galactose-rich polysaccharide (GRP) was prepared by mixing ten grams of solid agar (Bacteriological grade, purchased from DIFCO laboratories) with 100 mL of deionized water. After constant stirring for 1 hour, the soluble extract was passed through a sintered glass filter. The filtrate was dialyzed against distilled water, and the absorption maxima of the dialysate was determined using a UV spectrophotometer. The agar extract solution was freeze-dried and stored at room temperature.

A portion of the agar extract was hydrolyzed in 4M trifluoroacetic acid at 100° C. for 4 hours for carbohydrate analysis and the monosaccharides were quantitated as alditol acetates by gas-liquid chromatography. Chemical analysis revealed that the extract was composed mainly of galactose-derivatives. The relative molar proportions were as follows: galactose, 1; 3,6-anhydrogalactose, 0.2; 2-Ome-galactose, <0.05; 4-Ome-galactose, <0.05.

Preparation of Im-LF/LF mixture

A mixture of Im-LF and native LF was prepared by mixing a solution of GRP (1% wt/vol) in deionized water with LF (1% wt/vol), obtained from cheese-whey fractionation (also in deionized water) in a 1:100 ratio. The mixture was kept at room temperature with gentle stirring for 90 minutes. The formation of Im-LF was confirmed by gel-filtration chromatography using Sephacryl S-200 HR column.

Sample Preparation

Sterile solutions of citric acid, sodium bicarbonate, and GRP were prepared and 50 µl aliquots were added, each in duplicate, to the horizontal lanes of a sterile 96-well microtiter plate. A volume of 50 µl of bacterial suspension (about $10^3$ or $10^6$ cells/mL) prepared in saline, was added to each sample. Additionally, a sample was prepared containing a mixture of GRP, citric acid, sodium bicarbonate, and sodium chloride. Appropriate amounts of sterile deionized water was added to adjust the final volume of fluid in each well to 200 µl. The final concentration of each sample is reported in Table 1 below.

Im-LF/LF mixture samples were prepared in double-strength trypticase soy broth growth media and a volume of 100 µl of the resulting solutions was added, each in duplicate wells, to the vertical columns of the microtiter plate. A volume of 50 µl of bacterial suspension, about $10^3$ or $10^6$ cells/mL, prepared in saline, was added to the duplicate wells, respectively. Additionally, a mixture containing Im-LF/LF, citric acid, sodium bicarbonate, and sodium chloride was prepared. Appropriate amount of sterile deionized water was added to each sample to adjust the final volume of fluid in each well to 200 µl. The concentrations of each sample are reported in Table 1 below.

Sample Assay

All the samples, plus a control, were incubated at 37° C. The bacterial growth was monitored at different time intervals as turbidity change in culture media by measuring OD (optical density) at 600 nm in a microplate reader. Wells containing growth media without bacteria served as sterility control, whereas the wells with growth media and bacteria without test compounds served as positive growth control. The antimicrobial activity of a test substance was estimated as % growth relative to the positive growth control. The results after incubating the samples for 24 hours are reported in Table 1.

TABLE 1

| SAMPLE | GROWTH (%) |
| --- | --- |
| A) Control (trypticase soy broth) | 100 |
| B) 0.001 M citric acid | 103 |
| C) 0.01 M sodium bicarbonate | 112 |
| D) 0.1 M sodium chloride | 100 |
| E) 0.01% weight/volume GRP | 125 |
| F) Mixture of B + C + D + E | 125 |
| G) 1% LF | 36 |
| H) 1% Im-LF/LF mixture | 28 |
| I) 1% Im-LF/LF mixture in B + C + D | 0 |

Both the LF and Im-LF/LF mixture reduced the growth of the *E. coli*. However, the Im-LF/LF mixture in buffer solution totally inhibited such growth.

Example 2

An antimicrobial assay was performed using buffer solutions containing mixtures of 1% wt/vol LF and 1% wt/vol Im-LF or mixtures of 0.5% wt/vol LF and 0.5% wt/vol Im-LF 0.5% to demonstrate their ability to inhibit the growth-multiplication of different cell densities of *E. coli* O157:H7 strain ATCC43895.

GRP-immobilized 2% wt/vol Im-LF/native LF mixture was prepared in deionized water as described in Example 1 above. A buffer solution was prepared by combining citric acid (0.002M), sodium bicarbonate (0.02M), and sodium chloride (0.2M) in deionized water. The buffer solution was then sterilized by autoclaving.

The 1% mixture was then prepared by combining the Im-LF/native LF solution and the buffer solution, under aseptic conditions, at 1:1 ratio. The final composition of the 1% mixture is shown in TABLE 2.

TABLE 2

| native LF (1% wt/vol) | 10.00 g |
| --- | --- |
| Im-LF (1% wt/vol) | 10.00 g |
| GRP (1% wt/vol) | 10.00 mL |
| Citric acid (0.001 M) | 0.19 g |
| Sodium bicarbonate (0.01 M) | 0.84 g |
| Sodium chloride (0.1 M) | 5.8 g |
| Deionized water (adjusted to) | 1.00 liter |

A 0.5% mixture was prepared by adding additional deionized water to the 1% wt/vol mixture solution.

Samples were prepared as described in Example 1 above, except that four samples were made from each solution and the bacterial density of each solution was varied as reported in Table 3. An assay was performed according to the method described in Example 1.

The results shown in Table 3 are end-point data obtained after 24 hours of incubation at 37° C.

TABLE 3

| E. COLI | % GROWTH | | |
| --- | --- | --- | --- |
| DENSITY | Control | 0.5% Formulation | 1% Formulation |
| $10^4$ cells/mL | 100 | 0 | 0 |
| $10^5$ cells/mL | 100 | 0 | 0 |
| $10^6$ cells/mL | 100 | 8 | 0 |
| $10^7$ cells/mL | 100 | 27 | 11 |

It can be seen that the 0.5% mixture blocked the growth-multiplication of $10^5$ cells of *E. coli* O157:H7/mL for 24 hours and the 1% mixture demonstrated an increase of one-log antimicrobial activity and effectively blocked $10^6$ cells of *E. coli* O157:H7/ML for 24 hours.

Similar antimicrobial experiments were also performed and comparable results were obtained with an additional four *E. coli* O157:H7 strains from American Type Culture Collection: (1) ATCC43888, enterotoxigenic isolate that does not produce either shiga-like toxin I or II; (2) ATCC43889, fecal isolate from patient with hemolytic uremic syndrome and produces shiga-like toxin 11; (3) ATCC43890, enterotoxigenic isolate that produces shiga-like toxin I; (4) ATCC43894, fecal isolate from outbreak of hemorrhagic colitis and produces shiga like toxins I and II.

Example 3

An antimicrobial assay was performed using the 1% mixture prepared in accordance with Example 2 to demonstrate its ability to inhibit the growth-multiplication of different microorganisms. Samples were prepared as described in Example 1 above, except that two samples were made for each microbe to be tested and the bacterial density in the samples was $10^3$ and each $10^6$ cells/mL, respectively and that the growth media used for each bacteria varied as is reported in Table 4.

An assay was performed according to the method described in Example 2. The results are shown in Table 4 below. The microbial growth in the Control (Growth media) was considered as 100%.

TABLE 4

| MICROORGANISM | Control (Broth) | % GROWTH $10^3$ cells/ mL | $10^6$ cells/ mL |
|---|---|---|---|
| Enterotoxigenic *E. coli* H10407 | Tryptic-soy | 0 | 0 |
| Enteropathogenic *E. coli* | Tryptic-soy | 0 | 0 |
| *Shigella dysenteriae* | Tryptic-soy | 0 | 0 |
| *Shigella flexneri* SFL1070-15 | Tryptic-soy | 0 | 0 |
| *Salmonella typhimurium* R10 | Tryptic-soy | 0 | 0 |
| *Salmonella abony* NCTC6017 | Tryptic-soy | 0 | 0 |
| *Salmonella dublin* NCTC9676 | Tryptic-soy | 0 | 0 |
| *Salmonella hartford* HNCMB10063 | Tryptic-soy | 0 | 0 |
| *Salmonella kentucky* NCTC5799 | Tryptic-soy | 0 | 0 |
| *Salmonella panama* NCTC5774 | Tryptic-soy | 0 | 0 |
| *Salmonella pullorum* NCTC5776 | Tryptic-soy | 0 | 0 |
| *Salmonella rostock* NCTC5767 | Tryptic-soy | 0 | 0 |
| *Salmonella thompson* NCTC5740 | Tryptic-soy | 0 | 0 |
| *Salmonella virschow* NCTC5742 | Tryptic-soy | 0 | 0 |
| *Campylobacter jejuni* ATCC33560 | Brucella Albimi | 0 | 9 |
| *Yersinia enterocolitica* Y162 | Tryptic-soy | 0 | 0 |
| *Aeromonas hydrophila* CCUG14551 | Tryptic-soy | 0 | 0 |
| *Staphylococcus aureus* SA-43 | Nutrient | 0 | 12 |
| *Staphylococcus hyicus* AC-166 | Nutrient | 0 | 14 |
| *Staphylococcus epidermidis* AF-9 | Nutrient | 0 | 6 |
| *Staphylococcus hominis* AF-93 | Nutrient | 0 | 4 |
| *Staphylococcus warneri* AF-101 | Nutrient | 0 | 11 |
| *Staphylococcus xylosus* AG-12 | Nutrient | 0 | 8 |
| *Staphylococcus chromogenes* AD-1 | Nutrient | 0 | 20 |
| *Bacillus cereus* | Nutrient | 0 | 17 |
| *Bacillus subtilis* | Nutrient | 0 | 24 |
| *Candida albicans* | Saboraud | 0 | 8 |
| Radiation-resistant bacteria | | | |
| *Brochothrix thermospacta* ATCC11509 | Nutrient | 0 | 28 |
| *Bacillus pumilus* ATCC27142 | Tryptic-soy | 0 | 18 |
| *Enterococcus faecium* ATCC19579 | Brain-heart | 0 | 27 |
| *Deinococcus radiopugnans* ATCC19172 | Nutrient | 2 | 36 |
| *Deinococcus radiodurans* ATCC13939 | 1% Glu-Nutrient | 3 | 43 |
| *Deinobacter grandis* ATCC43672 | Tryptic-soy | 2 | 34 |
| *Acinetobacter radioresistens* ATCC43998 | Nutrient | 9 | 51 |
| *Methylobacterium radiotolerans* ATCC27329 | Nutrient | 7 | 45 |

The 1.0% mixture effectively inhibited all the potential Gram-negative food-borne pathogens at both cell densities. Total inhibition was demonstrated at a cell density of $10^3$ cells/mL. Near total inhibition, ranging from total inhibition to 75% inhibition, was demonstrated at a cell density of $10^6$ cells/mL.

Radiation-resistant *Brochothrix thermospacta, Bacillus pumilus* and newly emerging meat pathogen *Enterococcus faecium* was totally inhibited at $10^3$ cells/mL using the 1.0% mixture. The remaining five radiation-resistant species tested were inhibited at over 90% at the same cell densities. Inhibition of growth-multiplication demonstrated a range of about 82% to 49% at a higher density of $10^6$ cells/mL using the 1% mixture Example 4

The mode of action of antimicrobial formulations in accordance with the invention was demonstrated with *E. coli* O157:H7 strain ATCC43895 on various beef tissues.

Microbial Adhesion Assay

*E. coli* O157:H7, strain ATCC43895, was grown in tryptic soy broth at 37° C. overnight. A loopful of the resulting culture was inoculated into 5 mL of tryptic soy broth containing $^3$H-thymidine (20 Ci) and incubated for 7 hours at 37° C. to incorporate $^3$H-thymidine into the bacteria's DNA. The labeled *E. coli* were harvested by centrifugation and the cell density adjusted to an OD of 0.02 (approximately $10^7$ bacterial/mL) at 600 nm using a photometer. Total plate counts were simultaneously performed and a standard curve was plotted between bacterial counts and corresponding $^3$H-thymidine labeled bacterial radioactivity.

Two-mL volumes of $^3$H-labeled bacteria (about $2\times10^7$ cells) were incubated at room temperature in a 20-mL glass scintillation vial with approximately 0.4 g of beef tissue (four samples each of lean, fat or surface tissue from neck) to give the bacteria the opportunity to adhere to the tissue samples. After 2 hours, the non-adherent bacteria were aspirated into a second scintillation vial. Each of the three sets of samples containing the adherent bacteria were then treated with either water, saline (0.5%), lactic acid (2%), LF (1%), and the buffer solution containing 1% GRP-Im-LF and native LF in order to detach the tissue-adherent bacteria. The treatment solutions were aspirated into another scintillation vial. Finally, the treated tissue sample was digested with 2 mL of tissue homogenizer (Scintigest, Fisher Scientific) overnight at 55° C. in a waterbath-shaker. A 10-mL volume of scintillation cocktail (ScintiSafe Gel, Fisher Scientific) was added to the homogenate and the radioactivity (DPM, disintegrations per minute) was measured in a scintillation counter (Tri-Carb 2100TR, Packard Instruments). The results are shown in TABLE 5.

TABLE 5

| | % BACTERIAL CELLS DETACHED IN 1-MINUTE | | |
|---|---|---|---|
| WASH TREATMENT | Lean tissue | Fat tissue | Surface tissue (neck) |
| Water | 73 | 64 | 68 |
| Saline (0.5%) | 87 | 72 | 75 |
| Lactic acid (2%) | 75 | 68 | 62 |
| LF (1%) | 90 | 85 | 78 |
| Formulation (1%) | 99 | 96 | 94 |

Approximately, $10^4$ cells of *E. coli* O157:H7 were initially attached to each of the beef tissue samples. Wash with 1% LF solution demonstrated an effective bacterial detachment. The 1% formulation demonstrated a maximum bacterial detachment profile of 99% with lean tissues, 96% with fat tissues, and 94% with surface tissues from beef. Wash treatments lasting longer than 2 minutes using the 1% formulation demonstrated detachment profiles at 100%.

Similar results were obtained using four additional strains of *E. coli* O157:H7 from the American Type Culture Collection: (1) ATCC43888, (2) ATCC43889, (3) ATCC43890, and (4) ATCC43894.

Example 5

The efficacy of microbial detachment of *E. coli* O157:H7 from beef tissue using a buffer solution containing 1%

Im-LF and native LF was tested in a 10-second wash with a digitally simulated spray system (DS³).

Digitally Simulated Spray System

The DS³ was specially engineered to simulate the conditions of a beef processing plant. The DS³ consists of a programmable belt-line to carry meat through a total of 12 processing chambers including 6 spray-, 5 pause- and 1 meat loading-chambers. The spray chambers were connected to individual delivery tanks (2-gallon capacity) via digitally-controlled pumps with adjustable spray flow, spray time, pause, etc. These 6 spray chambers were connected into individual fluid collectors.

Sample Preparation

A meat tissue (about 4 sq. inch area) was fixed in the center of a stainless steel loading frame, located inside a beta-ray shielded acrylic box. A sterile bactainer, with an area of 1 sq. inch×0.5 inches in height and an open stainless steel hollow with a sharp-edged square end, was firmly pressed into the meat. A 5-mL volume of ³H-thymidine labeled E. coli O157:H7 cells (about 5×10⁷ cells) was inoculated onto the meat surface exposed inside the bactainer and the interaction was allowed for 2 hours at room temperature. The non-attached bacterial cells were aspirated into a scintillation vial. The bactainer was removed and the loading frame with ³H-thymidine labeled E. coli O157:H7 was removed from the acrylic box and mounted and locked on the meat-loading chamber of the equipment.

Sample Treatment

A set of three samples were treated with a sanitizing assembly treatment that simulated the time/temperature/spray pressure/pause typically employed during commercial beef slaughter processing. The sanitizing assembly consisted of five spray washing steps, 10-seconds each, consisting of spraying with: water, 2% lactic acid, hot water (180° F., for 30 seconds), water, and 2% lactic acid, respectively. Samples were also treated using the standard assembly with the addition of the 1% formulation in each step.

Sample Assay

After treatment, the loading frame was dismounted and placed in the beta-ray shielded acrylic box. Six random samples (about 0.5 g wt) were excised from the area previously inoculated with ³H-thymidine labeled E. coli O157:H7 cells. The samples were digested with 4 mL of tissue homogenizer (Scintigest, Fisher Scientific) overnight at 55° C. in a waterbath-shaker. A 10-mL volume of scintillation cocktail (ScintiSafe Gel, Fisher Scientific) was added to the homogenate and the radioactivity (DPM, disintegrations per minute) was measured in a scintillation counter (Tri-Carb 2100TR, Packard Instruments).

The results of the efficacy testing are shown in TABLE 6.

TABLE 6

| EXPERIMENT | % E. COLI O157:H7 DETACHMENT (PER GRAM TISSUE) | |
| --- | --- | --- |
| | Sanitizing Assembly | Sanitizing Assembly + 1% Formulation |
| Run-1 | 72.0% | 99.9% |
| Run-2 | 68.1% | 100.0% |
| Run-3 | 76.6% | 98.8% |
| Average | 72.2% | 99.6% |

The efficacy of a regular sanitizing assembly averaged 72.2% per g of beef tissue. The sanitizing assembly coupled with the 1% formulation spray demonstrated 100% efficacy in Run-2 with an average 99.6% E. coli detachment per gm of beef tissue, between three experimental runs.

The invention claimed is:

1. A composition of matter comprising a dispersion of isolated lactoferrin immobilized on a naturally occurring substrate via the N-terminus region of the lactoferrin, and native lactoferrin.

2. The composition in accordance with claim 1, wherein the concentration of immobilized lactoferrin and native lactoferrin in the dispersion is from about 0.05% wt/vol to about 2.5% wt/vol.

3. The composition in accordance with claim 1, wherein the molar ratio of immobilized lactoferrin to native lactoferrin is a ratio of from about 1:1 to about 1:10.

4. The composition in accordance with claim 1, wherein the molar ratio of immobilized lactoferrin to native lactoferrin is a ratio of from about 1:1 to about 1:5.

5. The composition in accordance with claim 1, wherein the composition comprises about 1% wt/vol immobilized lactoferrin and about 1% wt/vol native lactoferrin.

6. A composition of matter comprising an aqueous buffer solution containing a physiologically acceptable acid selected from the group consisting of oxalic acid, ethylenediamine tetraacetic acid, carbonic acid, and citric acid; a physiologically acceptable base; and a physiologically acceptable salt selected from the group consisting of calcium chloride, potassium chloride, and sodium chloride, wherein the ratio of acid to base to salt is 0.1 to 0.0001 M (acid): 1 to 0.001 M (base): 10 to 0.01 M (salt) and containing a mixture of native lactoferrin and isolated lactoferrin immobilized on a galactose-rich polysaccharide comprising mainly galactose residues and derivatized galactose residues, collagen, fibronectin, casein, mucin, heparan-sulfate, carrageenan, deoxyribonucleic acid, or adenosine triphosphate via the N-terminus region of the lactoferrin, in a native lactoferrin to isolated immobilized lactoferrin molar ratio of from about 1:1 to about 1:5 and in a concentration of from about 0.001 to about 2.5% wt/vol.

7. The composition in accordance with claim 6, wherein the lactoferrin is immobilized on a galactose-rich polysaccharide comprising mainly galactose residues and derivatized galactose residues.

8. The composition in accordance with claim 6, wherein the mixture comprises about 1% wt/vol immobilized lactoferrin and about 1% wt/vol native lactoferrin.

9. The composition in accordance with claim 6, wherein the physiologically acceptable acid is citric acid, the physiologically acceptable base is sodium bicarbonate and the physiologically acceptable salt is sodium chloride.

10. A method for inhibiting the microbial contamination of a composition subject to microbial contamination comprising treating the composition with an aqueous buffer solution containing a physiologically acceptable acid selected from the group consisting of oxalic acid, ethylenediamine tetraacetic acid, carbonic acid, and citric acid; a physiologically acceptable base; and a physiologically acceptable salt selected from the group consisting of calcium chloride, potassium chloride, and sodium chloride, wherein the ratio of acid to base to salt is 0.1 to 0.0001 M (acid): 1 to 0.001 M (base): 10 to 0.01 M (salt) and containing a mixture of native lactoferrin and isolated lactoferrin immobilized on a galactose-rich polysaccharide comprising mainly galactose residues and derivatized galactose residues, collagen, gelatin, fibronectin, casein, mucin, heparan-sulfate, carrageenan, deoxyribonucleic acid, or adenosine triphosphate via the N-terminus region of the lactoferrin, in a native lactoferrin to isolated immobilized lactoferrin molar ratio of from about 1:1 to about 1:5 and in a concentration of from about 0.001 to about 2.5% wt/vol.

11. The method in accordance with claim 10, wherein the lactoferrin is immobilized on galactose-rich polysaccharide comprising mainly galactose residues and derivatized galactose residues.

12. The method in accordance with claim 10, wherein the mixture comprises about 1% wt/vol immobilized lactoferrin and about 1% wt/vol native lactoferrin.

13. The method in accordance with claim 10, wherein the physiologically acceptable acid is citric acid, the physiologically acceptable base is sodium bicarbonate and the physiologically acceptable salt is sodium chloride.

14. The method of claim 10, wherein the microbe is bacterium, a fungus, a protozoan, or a virus.

15. The method in accordance with claim 10, wherein the microbe is enterotoxigenic *Escherichia coli*, enteropathogenic *Escherichia coli*, *Shigella dysenteriae*, *Shigella flexeri*, *Salmonella typhimurium*, *Salmonella typhi*, *Salmonella abony*, *Salmonella dublin*, *Salmonella enteritidis*, *Salmonella hartford*, *Salmonella kentucky*, *Salmonella panama*, *Salmonella pullorum*, *Salmonella rostock*, *Salmonella thompson*, *Salmonella virschow*, *Enterobacter aerogenes*, *Vibrio cholerae*, *Yersinia enterocolitica*, *Campylobacter jejuni*, *Aeromonas hydrophila*, *Staphylococcus aureus*, *Staphylococcus hyicus*, *Staphylococcus epidermidis*, *Staphylococcus hominis*, *Staphylococcus warneri*, *Staphylococcus xylosus*, *Staphylococcus chromogenes*, *Streptococcus pyogenes*, *Streptococcus pneumoniae*, *Streptococcus mutans*, *Streptococccus sanguis*, *Pediococcus acne*, *Bacillus cereus*, *Bacillus anthracis*, *Bacillus subtilis*, a *Brucella* species, *Listeria monocytogenes*, *Legionella pneumophila*, *Bordetella pertussis*, *Pseudomonas aeruginosa*, *Francisella tularensis*, *Candida albicans*, *Brochothrix thermospacta*, *Bacillus pumilus*, *Enterococcus faecium*, *Actinobacillus actinomycetemcomitans*, *Porphyromonas gingivalis*, *Prevotella intermedia*, *Deinococcus radiopugnans*, *Deinococcus radiodurans*, *Deinobacter grandis*, *Acinetobacter radioresistens*, or *Methylobacterium radiotolerans*.

16. The method in accordance with claim 10, wherein the microbe is a verotoxic *Escherichia coli*.

17. The method in accordance with claim 16, wherein the verotoxic *Escherichia coli* is the serotype 0157:H7.

18. The method of claim 10, wherein the microbe is a *Clostridium* sp.

19. The method of claim 18, wherein the species is *Clostridium perfringens*, *Clostridium difficile*, *Clostridium botulinum*, or *Clostridium tetani*.

20. The method in accordance with claim 10, wherein the ratio of acid to base to salt is 0.01 to 0.001 M (acid): 0.1 to 0.01 M (base):1 to 0.1 M(salt).

21. The method in accordance with claim 10, wherein the composition subject to microbial contamination is a foodstuff.

22. The method in accordance with claim 21, wherein the composition is a meat product.

23. The method of claim 22, wherein the meat product is a beef product, a pork product, or a poultry product.

24. The method of claim 22, wherein the meat product is veal, lamb, sheep, goat, elk, deer, antelope, horse, or dog.

25. The method of claim 21, wherein the foodstuff comprises a surface and/or flesh of a marine or freshwater aquatic organism.

26. The method of claim 25, wherein the aquatic organism is a fish, mollusk, or crustacean.

27. The method of claim 21, wherein the composition comprises a vegetable foodstuff.

28. A method for reducing the microbial contamination of a meat product subject to microbial contamination by a microbe, comprising: applying to the meat product a composition containing a physiologically acceptable acid selected from the group consisting of oxalic acid, ethylenediamine tetraacetic acid, carbonic acid, and citric acid; a physiologically acceptable base; and a physiologically acceptable salt selected from the group consisting of calcium chloride, potassium chloride, and sodium chloride, wherein the molar ratio of acid to base to salt is 0.1 to 0.0001 (acid): 1 to 0.001 (base): 10 to 0.01 (salt) and containing a mixture of native lactoferrin and isolated lactoferrin immobilized on a galactose-rich polysaccharide comprising mainly galactose residues and derivatized galactose residues, collagen, gelatin, fibronectin, casein, mucin, heparan-sulfate, carrageenan, deoxyribonucleic acid, or adenosine triphosphate via the N-terminus region of the lactoferrin, in a native lactoferrin to isolated immobilized lactoferrin molar ratio of from about 1:1 to about 1:5 and in a concentration of from about 0.001 to about 2.5% wt/vol.

29. The method of claim 28, wherein the composition is an aqueous solution, an aqueous emulsion, a colloid, a suspension, a powder, or a granular solid.

30. The method in accordance with claim 28, wherein the lactoferrin is immobilized on a galactose-rich polysaccharide comprising mainly galactose residues and derivatized galactose residues.

31. The method in accordance with claim 28, wherein the mixture comprises about 1% wt/vol immobilized lactoferrin and about 1% wt/vol native lactoferrin.

32. The method in accordance with claim 28 wherein the physiologically acceptable acid is citric acid, the physiologically acceptable base is sodium bicarbonate and the physiologically acceptable salt is sodium chloride.

33. The method of claim 28, wherein the microbe is a bacterium, a fungus, a protozoan, or a virus.

34. The method in accordance with claim 28, wherein the microbe is enterotoxigenic *Escherichia coli*; enteropathogenic *Escherichia coli*, *Shigella dysenteriae*, *Shigella flexneri*, *Salmonella typhimurium*, *Salmonella typhi*, *Salmonella abony*, *Salmonella dublin*, *Salmonella enteritidis*, *Salmonella hartford*, *Salmonella kentucky*, *Salmonella panama*, *Salmonella pullorum*, *Salmonella rostock*, *Salmonella thompson*, *Salmonella virschow*, *Enterobacter aerogenes*, *Vibrio cholerae*, *Yersinia enterocolitica*, *Campylobacter jejuni*, *Aeromonas hydrophila*, *Staphylococcus aureus*, *Staphylococcus hyicus*, *Staphylococcus epidermidis*, *Staphylococcus hominis*, *Staphylococcus warneri*, *Staphylococcus xylosus*, *Staphylococcus chromogenes*, *Streptococcus pyogenes*, *Streptococcus pneumoniae*, *Streptococcus mutans*, *Streptococccus sanguis*, *Pediococcus acne*, *Bacillus cereus*, *Bacillus anthracis*, *Bacillus subtilis*, a *Brucella* species, *Listeria monocytogenes*, *Legionella pneumophila*, *Bordetella pertussis*, *Pseudomonas aeruginosa*, *Francisella tularensis*, *Candida albicans*, *Brochothrix thermospacta*, *Bacillus pumilus*, *Enterococcus faecium*, *Actinobacillus actinomycetemcomitans*, *Porphyromonas gingivalis*, *Prevotella intermedia*, *Deinococcus radiopugnans*, *Deinococcus radiodurans*, *Deinobacter grandis*, *Acinetobacter radioresistens*, or *Methylobacterium radiotolerans*.

35. The method in accordance with claim 28, wherein the microbe is a verotoxic *Escherichia coli*.

36. The method in accordance with claim 35, wherein the verotoxic *Escherichia coli* is the serotype 0157: H7.

37. The method of claim 28, wherein the microbe is a *Clostridium* species.

38. The method of claim 37, wherein the species is *Clostridium perfringens, Clostridium difficile, Clostridium botulinum,* or *Clostridium tetani.*

39. The method in accordance with claim 28 wherein the concentration of lactoferrin on the surface of the meat product is from about 0.0001 to about 10 mg/sq. inch.

40. The method in accordance with claim 28, wherein the concentration of lactoferrin on the surface of the meat product is from about 0.01 to about 1 mg/sq. inch.

41. The method in accordance with claim 28, wherein the meat product is a beef product, a pork product, or a poultry product.

42. The method of claim 28, wherein the meat product is veal, lamb, sheep, goat, elk, deer, antelope, horse, or dog.

43. A foodstuff containing: isolated lactoferrin immobilized on a naturally occurring substrate via the N-terminus region of the lactoferrin in a concentration between about 0.0001 and about 10 mg per gram of the foodstuff.

44. The foodstuff of claim 43, wherein the foodstuff comprises a vegetable foodstuff.

45. A method of inhibiting the growth and/or adhesion of a microbial species on a foodstuff, comprising: treating a food-contacting surface of a material for food packaging or food handling with an isolated lactoferrin immobilized on a naturally occurring substrate via the N-terminus region of the lactoferrin; and contacting a foodstuff with said surface, whereby the growth and/or adhesion of a microbial species on said foodstuff is inhibited.

46. The method of claim 45, wherein said food packaging or handling material is a cellulosic polymer.

47. The method of claim 45, wherein said food packaging or handling material is paper, wood, or cardboard.

48. The method of claim 45, wherein said food-contacting surface comprises a surface belonging to a shear wrap, a cellophane, a wrapping paper, a waxed paper, a bag, a carton, a box, a tray, a plate, a bowl, a food storage vessel, a serving dish, a cup, a bin, a jar, or a bottle.

49. The method of claim 45, wherein said food-contacting surface comprises a surface belonging to a glove, a mitt, a fork, a spoon, a knife, a slicer, a tong, a ladle, a scoop, a cup, a processor, a juicer, a grinder, a press, a hook, a chipper, a peeler, a cutter, a screw, an opener, a chute, a spatula, a cutting board, a kneading board, a rack, or a shelf.

50. A food container or food-handling implement, said container or implement having a food-contacting surface, said surface treated with an isolated lactoferrin immobilized on a naturally occurring substrate via the N-terminus region of the lactoferrin in an amount effective to inhibit the growth and/or adhesion of a microbial species on said surface.

51. The food container or food-handling implement of claim 50, wherein said container or implement is a shear wrap, a cellophane, a wrapping paper, a waxed paper, a bag, a carton, a box, a tray, a plate, a bowl, a food storage vessel, a serving dish, a cup, a bin, a jar, a bottle, a glove, a mitt, a fork, a spoon, a knife, a slicer, a tong, a ladle, a scoop, a processor, a juicer, a grinder, a press, a hook, a chipper, a screw, a cutter, a peeler, an opener, a chute, a spatula, a cutting board, a kneading board, a rack, or a shelf.

52. The food container or food-handling implement of claim 50, having an amount of between about 0.0001 to about 10 mg/square inch of said food-contacting surface.

53. The composition in accordance with claim 6, wherein the molar ratio of acid to base to salt is 0.01 to 0.001 M (acid): 0.1 to 0.01 M (base): 1 to 0.1 M(salt).

* * * * *